(12) United States Patent
Evelyn et al.

(10) Patent No.: US 12,380,979 B2
(45) Date of Patent: Aug. 5, 2025

(54) SYSTEM AND METHOD FOR MONITORING AND MANAGING PATIENTS UNDERGOING IMMUNOTHERAPY

(71) Applicant: Alerje, Inc., Detroit, MI (US)

(72) Inventors: Javier Evelyn, Kalamazoo, MI (US); William Hunter Martin, Detroit, MI (US); Dustin Kang, Detroit, MI (US)

(73) Assignee: ALERJE, INC, Detroit, MI (US)

( * ) Notice: Subject to any disclaimer, the term of this patent is extended or adjusted under 35 U.S.C. 154(b) by 169 days.

(21) Appl. No.: 17/377,063

(22) Filed: Jul. 15, 2021

(65) Prior Publication Data

US 2022/0020467 A1    Jan. 20, 2022

Related U.S. Application Data

(60) Provisional application No. 63/122,049, filed on Dec. 7, 2020, provisional application No. 63/052,724, filed on Jul. 16, 2020.

(51) Int. Cl.
*G16H 20/17* (2018.01)
*A61B 5/00* (2006.01)
(Continued)

(52) U.S. Cl.
CPC .......... *G16H 20/17* (2018.01); *A61B 5/0002* (2013.01); *G06Q 50/26* (2013.01);
(Continued)

(58) Field of Classification Search
CPC ........ G16H 10/60; G16H 20/60; G16H 40/20; G16H 40/67; A61B 5/0002; H04L 67/12; G06Q 50/26; G07C 9/00182
(Continued)

(56) References Cited

U.S. PATENT DOCUMENTS

| | | | |
|---|---|---|---|
| 2005/0197621 A1 | 9/2005 | Poulsen et al. | |
| 2013/0302374 A1* | 11/2013 | Esch | A61K 39/36 435/29 |

(Continued)

FOREIGN PATENT DOCUMENTS

| | | | | |
|---|---|---|---|---|
| CN | 208229182 U | * | 12/2018 | ............. A47G 21/00 |
| WO | WO-2007064924 A1 | * | 6/2007 | ......... A61N 1/37211 |

(Continued)

OTHER PUBLICATIONS

Numlil Khaira Rusd; Cancer Immunotherapy and Flow Cytometry in Immunotherapy Monitoring; Biomedical & Pharmacology Journal 12.3: 1587-1593. Biomedical and Pharmacology Journal.( 2019) (Year: 2019).*

(Continued)

*Primary Examiner* — Hiep V Nguyen
(74) *Attorney, Agent, or Firm* — The Dobrusin Law Firm, P.C.

(57) ABSTRACT

The present teachings generally relate to a system and method for managing medical treatment. The system comprises one or more devices including a patient device and one or more physician devices, the one or more devices including: one or more user interfaces, and one or more network modules; and a medical network; wherein the patient device receives, from a patient and/or one or more caregivers, patient data including food journal data, quality of life data, medication data, or any combination thereof; wherein the patient device transmits the patient data to the one or more physician devices; and wherein the patient data is utilized by one or more physicians to adjust a dosage quantity and/or a dosage frequency of food allergy immunotherapy medication.

17 Claims, 14 Drawing Sheets

(51) Int. Cl.
    *G06Q 50/26*     (2024.01)
    *G07C 9/00*     (2020.01)
    *G16H 10/60*     (2018.01)
    *G16H 20/60*     (2018.01)
    *G16H 40/20*     (2018.01)
    *G16H 40/67*     (2018.01)
    *H04L 67/12*     (2022.01)

(52) U.S. Cl.
    CPC ......... *G07C 9/00182* (2013.01); *G16H 10/60* (2018.01); *G16H 40/20* (2018.01); *G16H 40/67* (2018.01); *H04L 67/12* (2013.01); *G16H 20/60* (2018.01)

(58) Field of Classification Search
    USPC ............................................................ 705/2
    See application file for complete search history.

(56) References Cited

U.S. PATENT DOCUMENTS

| | | | |
|---|---|---|---|
| 2015/0216413 A1* | 8/2015 | Soyao | H04L 67/12 |
| | | | 709/204 |
| 2015/0250956 A1* | 9/2015 | Ostrander | G16H 10/65 |
| | | | 604/111 |
| 2017/0329917 A1 | 11/2017 | McRaith et al. | |
| 2019/0366001 A1 | 12/2019 | Evelyn et al. | |

FOREIGN PATENT DOCUMENTS

| | | | | |
|---|---|---|---|---|
| WO | WO-2014159609 A1 * | 10/2014 | ............. | A23L 25/30 |
| WO | WO-2020237181 A1 * | 11/2020 | ............. | A23L 25/00 |

OTHER PUBLICATIONS

International Search Report and Written Opinion dated Nov. 15, 2021 for International Application PCT/US21/41848.
Extended European Search Report, EP Application No. 21 842 684 dated Jul. 1, 2024.

* cited by examiner

| Time | Event 161 | Category 164 |
|---|---|---|
| 7AM | Wake up | Occupied event 172 |
| 7AM-9AM | Morning routine & commute | Occupied event 172 |
| 9AM-4PM | School | Occupied event 172 |
| 4PM-5PM | Soccer practice | Risk event 170 |
| 6PM-7PM | Homework | Controlled event 168 |
| 7PM-9PM | | |
| 9PM | Bedtime | Occupied event 172 |

SYSTEM AND METHOD FOR MONITORING AND MANAGING PATIENTS UNDERGOING IMMUNOTHERAPY

FIELD

The present teachings generally relate to a medical treatment management system. The medical treatment management system may be particularly advantageous in managing patients undergoing immunotherapy for food allergies.

BACKGROUND

At present, about 32 million Americans suffer from food allergies. Food allergies burden the lifestyles of those afflicted. Individuals with food allergies have to closely monitor their diets, seek out allergen-free foods on restaurant menus, constantly carry medication on their person, bear the costs of medication and medical treatment, and suffer from general anxiety of the possibility of experiencing an adverse reaction. Despite the precautions undertaken by afflicted individuals, about 200,000 Americans are hospitalized annually and about 150-200 Americans die annually due to food allergies.

Immunotherapy is a preventative treatment for food allergies that involves gradually increasing the quantity and frequency of doses of an allergen to a patient. Immunotherapy is administered in several different forms including oral immunotherapy ("OIT"), epicutaneous immunotherapy ("EPIT"), and sublingual immunotherapy ("SLIT"). OIT involves oral doses of allergens. EPIT involves skin exposure of allergens by an adhesive dermal patch. SLIT involves tablets or droplets of allergens administered under the tongue. Immunotherapy for food allergies is a developing field of medicine and as a result, new medications directed to different allergens are incrementally approved by the U.S. Food and Drug Administration ("FDA") and made available in the consumer market. As with most medical treatments, FDA approval and entrance into the consumer market is only the beginning to determining efficacy and safety. Widescale studies controlling for a variety of variables are still needed to determine efficacy and safety of treatments.

Some medications are approved by the FDA contingent on the medication producer developing a program known as a Risk Evaluation Mitigation Strategy ("REMS"). A REMS is designed to monitor, manage, and inform of serious risks borne by the patient. For instance, a REMS may include a requirement that a medication can only be administered in a certified medical care facility. Some immunotherapy medications carry with them a REMS requirement.

Patients undergoing immunotherapy are not free from the burdens of their food allergies and in some cases, they may have increased burdens as a result of the immunotherapy. Patients have to purchase expensive immunotherapy medication, visit physicians more frequently than normal for routine monitoring and dose modifications, make lifestyle changes to accommodate medication dosing schedules, and expose themselves to adverse reactions upon ingesting the medication. Some patients may be dissuaded from participating in immunotherapy altogether and as a result, the population from which data is drawn to study immunotherapy efficacy may be limited. Other patients may begin immunotherapy but stop due to the aforementioned burdens. Thus, the long-term market viability of immunotherapy may be limited. Even other patients may undertake immunotherapy but undergo cycles of compliance and non-compliance with medical guidelines, thereby skewing the perceived efficacy of the treatment.

Currently, there is a shortage of allergists in the United States. Patients undergoing immunotherapy are recommended to visit allergists at a higher frequency to monitor the progress of the treatment. Patients also are urged to schedule appointments after adverse reactions so that dosage may be adjusted. However, while said dosage adjustment should be undertaken as soon as possible after an adverse reaction, scheduling capacities of allergists may be limited to the effect of delaying dosage adjustment appointments for days or even weeks after an adverse reaction takes place. This increased load on the current capacity of allergists presents a challenge for accommodating an expanding amount of immunotherapy patients. In addition, patients may be inconvenienced by the increased incidence of office visits. Patients living in rural areas remote from an allergist are particularly afflicted by the increase in office visits due to long commutes.

Patient data may be used by physicians, pharmaceutical companies, and insurance companies to enhance various aspects of treatment management, efficacy, medical guidelines, pricing, and the like. However, currently there are limitations as to the collection, storage, access, and analysis of patient data. Manual input of data, by patients, is time consuming and accordingly the breadth of data collected may be limited by patient's schedules, the willingness of patients to set aside time to input a large volume of data, and patients remembering to input data on a regular basis. Physicians may use patient data to drive treatment management, however navigating through raw data is a time-consuming process and may not unlock all of the potential that the raw data has to offer without intermediate and automated processing and analysis steps performed prior to the physician's review. Pharmaceutical companies may use patient data to alter medication formulations and medical guidelines issued to physicians. However, current direct access to such data by pharmaceutical companies is limited. Furthermore, pharmaceutical companies require a high level of data integrity, population size, and resolution to reliably act in response to the data. Pharmaceutical companies may also require an increased breadth of the types of data collected to extract meaningful conclusions from the data. For example, it may not be enough to ascertain merely whether or not a patient has an adverse reaction; the pharmaceutical company may need to know whether an adverse reaction resulted from the medication itself, accidental ingestion of a food containing an allergen, or a combination of both factors. Insurance companies may use patient data to determine pricing of and coverage for the medication. However, current direct access to such data by insurance companies is limited.

It would be desirable to provide a system and method for collecting data from patients undergoing immunotherapy to indicate the efficacy of treatment.

It would be desirable to provide a system and method for monitoring, managing, and informing patients that would satisfy the FDA's REMS requirement.

It would be desirable to provide a system and method for assisting patients manage treatment, minimize the impact of the treatment on the patient's lifestyle, and alleviate anxieties associated with adverse reactions.

It would be desirable to provide a system and a method for encouraging patients maintain consistent compliance with medical guidelines while on the treatment.

It would be desirable to provide a system and a method for remotely connecting immunotherapy patients with allergists.

It would be desirable to provide a system and method for automating at least a portion of data entry so that data integrity and volume is maximized without imposing the burdens of manual data entry on patients.

It would be desirable to provide a system and method for collecting and storing data and providing access to said data by physicians, pharmaceutical companies, and insurance companies.

SUMMARY

The present disclosure relates to a system for managing medical treatment, which may address at least some of the needs identified above, the system comprising: one or more devices including a patient device and one or more physician devices, the one or more devices including: one or more user interfaces, and one or more network modules; and a medical network; wherein the patient device receives, from a patient and/or one or more caregivers, patient data including food journal data, quality of life data, medication data, or any combination thereof; wherein the patient device transmits the patient data to the one or more physician devices; and wherein the patient data is utilized by one or more physicians to adjust a dosage quantity and/or a dosage frequency of food allergy immunotherapy medication.

The present disclosure relates to a non-transitory computer-readable storage medium storing an application, the computer-readable storage medium comprising instructions for a method for managing medical treatment, which may address at least some of the needs identified above, the method comprising: receiving, by one or more remote devices and/or a patient device from one or more physician devices, medication data including a dose quantity, a dose frequency, or both; retrieving, by the one or more remote devices and/or the patient device from one or more databases, one or more adjustment parameters; and calculating, by the one or more remote devices and/or the patient device, an adjusted dose quantity, an adjustment dose frequency, or both based upon the one or more adjustment parameters; wherein the medication data is associated with a food allergy immunotherapy medication.

The present disclosure relates to a non-transitory computer-readable storage medium storing an application, the computer-readable storage medium comprising instructions for a method for assisting a patient in need of medical attention, which may address at least some of the needs identified above, the method comprising: receiving, by a patient device from a medication device, a signal, the signal indicating use of the medication device by the patient; generating, by the patient device, a communication, in response to the signal, the communication indicating the patient is in need of the medical attention; and transmitting, by the patient device, the communication to one or more emergency services.

BRIEF DESCRIPTION OF THE DRAWINGS

FIG. 12 illustrates a graphical user interface.
FIG. 13A illustrates a graphical user interface.
FIG. 13B illustrates a graphical user interface.
FIG. 16 illustrates a graphical user interface.
FIG. 17 illustrates a graphical user interface.
FIG. 18 illustrates a graphical user interface.

DETAILED DESCRIPTION

Figure 1:
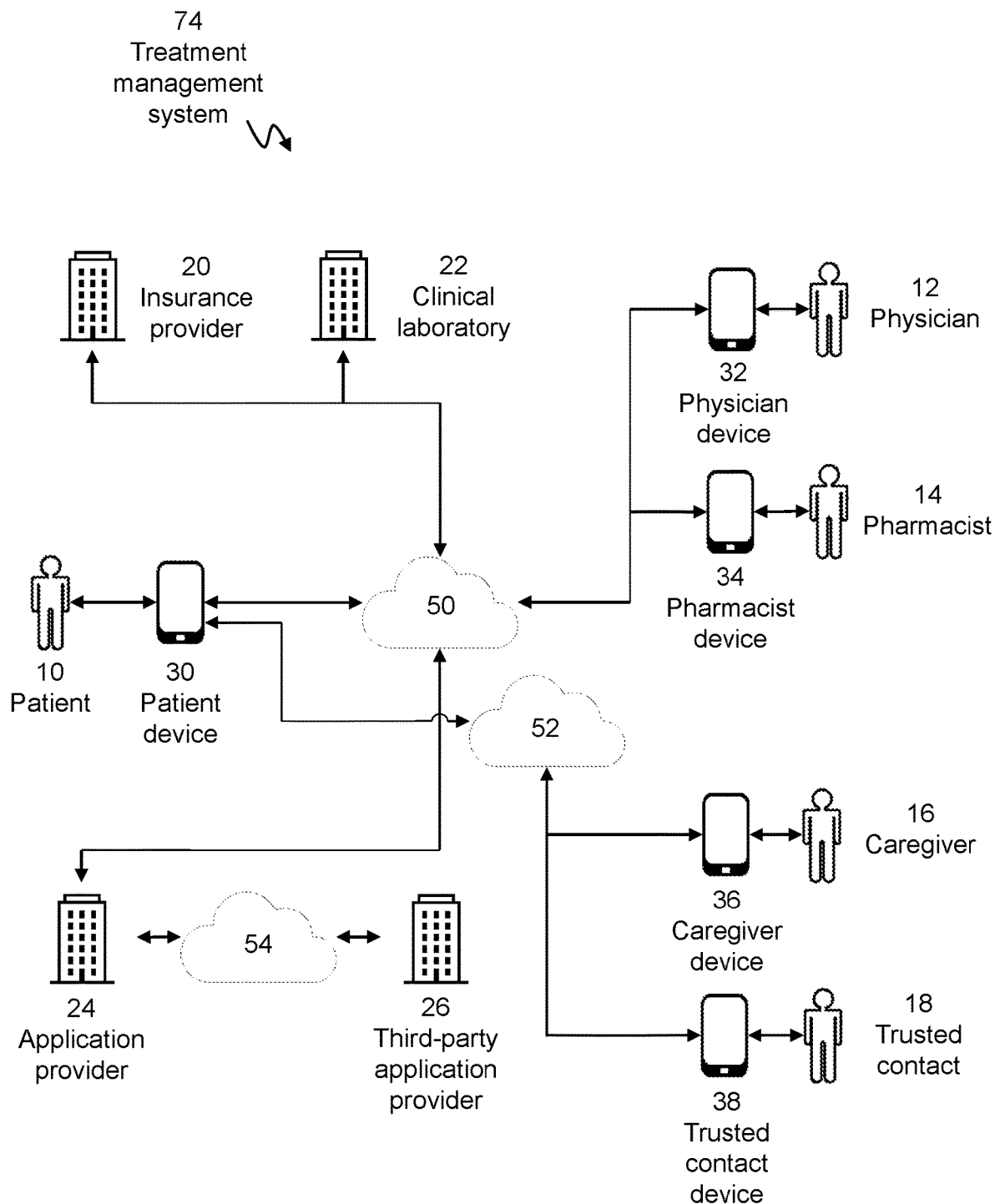
FIG. 1 is a schematic of a treatment management system.

The present teachings meet one or more of the above needs by the improved system and method described herein. The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

A. Patient and Related Parties

The system and method of the present disclosure may communicationally connect patients undergoing medical therapy with various parties, including the patient's physician, and provide information sharing mechanisms. The system and method may collect patient data from the patient, manually and/or automatically, and utilize the patient data for scholarly treatment studies, to formulate individual medical guidelines for the patient, to modify existing clinical standard guidelines, present the information back to the patient to gamify the medical therapy, or any combination thereof. The system and method may collect data from various sources and provide the patient access to the data. For example, access to scholarly journals regarding a patient's particular type of medical therapy may be provided to the patient. The system and method may perform one or any combination of the aforementioned functions while minimizing the footprint of patient interaction with the system and method. For example, a variety of data may be collected autonomously from the patient. As referred to herein, "autonomous" may mean without human direction or interaction with a device. As another example, data may be obtained from other applications to avoid redundancy in data entry. As yet another example, the data may be utilized for machine learning ("artificial intelligence") to tailor the system and method to the patient's lifestyle.

The system and method of the present disclosure may be used by one or more patients. Patient may be alternatively referred to herein as a user. The one or more patients may be any person undergoing medical therapy. The one or more patients may include any person with a food allergy. The medical therapy may involve the ingestion, injection, or absorption of a medication. The medical therapy may include immunotherapy, cancer treatments, autoimmune treatments, viral treatments, the like, or any combination thereof. The immunotherapy may include cancer immunotherapy, autologous immune enhancement therapy, autoimmune disorder immunotherapy, food allergy immunotherapy, the like, or any combination thereof. The patient may include a child, a teenager, an adult, or any combination thereof.

The food allergy immunotherapy may include oral immunotherapy ("OIT"), epicutaneous immunotherapy ("EPIT"), and sublingual immunotherapy ("SLIT"). The food allergy immunotherapy may involve exposing a patient to a quantity of allergen below a threshold (i.e., the threshold below which would not induce an adverse reaction by the patient) and incrementally increasing the quantity of the allergen with the goal of desensitizing the immune system of the patient. The medical therapy may be personalized to individual patients. The medical therapy may be personalized based on an individual's overall health profile, age, gender, genetics, treatment goals, progress throughout treatment, or any combination thereof. The medical therapy may be personalized before the start of therapy, during therapy, or both.

While the present teachings are presented with discussion and examples directed to oral immunotherapy for food allergies, the system and method of the present disclosure may be utilized for any type of medical treatment in which treatment persists for an extended period of time and requires both patient action (e.g., daily medication intake) as well as patient feedback.

The medical therapy may be administered and/or monitored by one or more physicians. The physicians may interact with and/or exchange information with one or more patients, pharmacists, caregivers, insurance providers, clinical laboratories, or any combination thereof via the system and method of the present disclosure. The physicians may include a primary care physician, an allergist, a psychiatrist, the like, or any combination thereof.

The medical therapy may be administered and/or monitored by one or more pharmacists. The pharmacists may interact with and/or exchange information with one or more patients, physicians, caregivers, insurance providers, clinical laboratories, or any combination thereof via the system and method of the present disclosure. The pharmacists may fulfill prescriptions, provided by the one or more physicians, for the one or more patients. The prescriptions may include prescriptions for immunotherapy medications. The one or more pharmacists may provide over-the-counter ("OTC") medications to the one or more patients.

The one or more patients may have one or more caregivers. The caregivers may interact with and/or exchange information with one or more patients, physicians, pharmacists, trusted contacts, insurance providers, clinical laboratories, or any combination thereof via the system and method of the present disclosure. The caregivers may assist and/or oversee a patient with their medical treatment. The caregivers may monitor the one or more patients and/or respond to a medical emergency of the one or more patients. The medical emergency may include an adverse reaction, anaphylaxis, or both. The caregivers may include a professional caregiver or a familial caregiver. The professional caregiver may include an elderly caregiver, a disability caregiver, the like, or any combination thereof. The familial caregiver may include biological parents, adoptive parents, foster parents, legal guardians, the like, or any combination thereof.

The one or more patients may have one or more trusted contacts. The trusted contacts may interact with and/or exchange information with a patient, one or more caregivers, or both via the system and method of the present disclosure. The trusted contacts may monitor a patient and/or respond to a medical emergency of the patient. The medical emergency may include an adverse reaction, anaphylaxis, or both. The trusted contacts may include family, friends, neighbors, professional colleagues, the like, or any combination thereof.

The system and method of the present disclosure may be used by one or more insurance providers. The insurance providers may interact with and/or exchange information with one or more patients, physicians, pharmacists, caregivers, clinical laboratories, or any combination thereof via the system and method of the present disclosure. The insurance providers may provide the one or more patients with medical insurance. The insurance providers may cover the costs for the medication used in connection with the therapy. The insurance providers may have a financial interest in the adherence of the patients to the medical guidelines and/or the efficacy of the therapy. Adherence by the patients and/or efficacy of the therapy may be a contingency for the insurance providers to cover the at least some of the costs of the medication used in connection with the therapy. The one or more insurance providers may have access to at least some data associated with all of the past and/or current patients using the treatment management system.

The system and method of the present disclosure may be used by one or more clinical laboratories. The clinical laboratories may interact with and/or exchange information with one or more patients, physicians, pharmacists, caregivers, insurance providers, or any combination thereof via the system and method of the present disclosure. The clinical laboratories may conduct biological sample collection on patients and/or carry out pathological tests on biological samples collected from patients. The one or more clinical laboratories may provide results of pathological tests to one or more patients, physicians, pharmacists, caregivers, insurance providers, or any combination thereof.

The system and method of the present disclosure may be provided and/or administered by one or more application providers. The application providers may provide the hardware and/or software to support an application. The application providers may interact with one or more patients, physicians, pharmacists, caregivers, trusted contacts, insurance providers, clinical laboratories, third-party application providers, or any combination thereof via the system and method of the present disclosure. The application providers may administer a database that exchanges information with and/or is accessible by one or more patients, physicians, pharmacists, caregivers, trusted contacts, insurance providers, clinical laboratories, third-party application providers, or any combination thereof. For example, the database may receive patient data from a patient that is accessible by a physician. The one or more application providers may have access to data associated with all of the past and/or current patients using the treatment management system.

As referred to herein, application may mean a computer program stored on computer-readable storage media that may be interacted with by a user. The application may include a computer-based application, a web-based application, or both. As referred to herein, "computer-based application" may mean a program stored locally on a device; and a "web-based application" may mean a program stored on a remote server and accessed by a device via a network.

The system and method of the present disclosure may include one or more third-party application providers. The third-party application providers may administer applications and databases having data that may be utilized by the system and method of the present disclosure. For example, a third-party application provider may administer a calendar application and the system and method of the present disclosure may request and/or receive data from the calendar application. The third party application providers may administer a calendar application, a text message application, a phonebook application, a phone application, an email application, a recipe application, a 2D code scanner application, a news application, a scholarly journal application, a government regulatory application, a medical information application, a diagnostic device application, a location services application, the like, or any combination thereof. The application provider may communicate with one or more third-party application providers, databases administered by the one or more third-party application providers, or both via an application programming interface ("API").

The system and method of the present disclosure may be used by one or more pharmaceutical companies. The pharmaceutical companies may provide commercially available medications or may be in the process of developing commercially available medications for the medical treatment undertaken by the patient. The pharmaceutical companies may use data collected and/or generated by the treatment management system of the present teachings for medication research and development. The one or more pharmaceutical companies may have access to at least some data associated with all of the past and/or current patients using the treatment management system. The pharmaceutical companies may use data collected and/or generated by the treatment management system of the present teachings to generate benefits for patients. Benefits for patients may be derived from and/or proportional to compliance, by patients, with medical guidelines associated with treatment. Benefits for patients may be derived from and/or proportional to the usage, by patients, of the application of the present disclosure. The benefits may include discounts, promotions, trials for alternative medicinal products, or any combination thereof.

The pharmaceutical companies may use data generated by the treatment management system of the present teachings to determine adherence, by patients, to medical guidelines associated with medical treatment. The adherence may be determined from an adherence parameter, food journal entries, medication entries, quality of life entries, or any combination thereof. The pharmaceutical companies may use data generated by the treatment management system to determine opinions, of patients, associated with the treatment. The opinions of the treatment may be determined from quality of life data. The pharmaceutical companies may use data generated by the treatment management system to determine behaviors of patients. The behaviors of the patients may be determined from patient data.

The application providers may communicate with the pharmaceutical companies via an application programming interface ("API"). The pharmaceutical companies may obtain patient data, derivative data, or both from the application providers via an API. Derivative data may mean data obtained by applying one or more algorithms and/or rules on patient data.

The system and method of the present disclosure may obtain data from one or more independent data sources. The one or more independent data sources may conduct research, conduct experimental drug trials, collect publicly and/or privately available data, or any combination thereof. The one or more independent data sources may include universities, research organizations, scholarly journal publishers, advocacy groups, or any combination thereof. The data provided by the independent data sources may include results of clinical studies, statistics, lists of allergens, chemical properties of allergens, biological properties of allergens, the like, or any combination thereof. The system and method of the present disclosure may utilize data from one or more independent data sources to implement and improve machine learning, inform patients, or both.

B. System and Hardware

The present disclosure provides for a treatment management system. The treatment management system may function to connect and provide a virtual interface between one or more patients, physicians, pharmacists, caregivers, trusted contacts, insurance providers, clinical laboratories, application providers, third-party application providers, or any combination thereof. The treatment management system may include one or more devices, user interfaces, processors, memory storage media, network modules, networks, databases, or any combination thereof. The treatment management system may provide for the exchange of data and/or information between one or more devices via one or more network modules. The treatment management system may provide for the exchange of data and/or information between one or more databases. The treatment management system may include a telehealth module, a monitoring module, a medical information module, or any combination thereof.

The treatment management system may include a telehealth module. The telehealth module may function to connect the one or more patients with one or more physicians, pharmacists, insurance providers, clinical laboratories, or any combination thereof.

The telehealth module may be a framework by which patient data may be relayed to one or more privileged parties. The privileged parties may include licensed medical professionals, persons with whom the one or more patients have contracted with, persons who have legal privileges with respect to the patient's medical information, or any combination thereof. The telehealth module may comprise a framework by which the privileged parties may relay and/or receive data to the patients. For example, a physician may relay medical guidelines and recommendations to a patient via the telehealth module. As another example, a pharmacist may receive prescriptions from a patient and/or physician from the telehealth module.

The telehealth module may comprise one or more devices, networks, or both. The telehealth module may comprise one or more patient devices, physician devices, pharmacist devices, or any combination thereof. The one or more devices may include one or more user interfaces, network modules, or both. The one or more user interfaces may receive data, relay data, or both. The one or more user interfaces may enable the parties to communicate with each other. The parties may communicate visually (e.g., video), audibly (e.g., microphone and speakers), textually (e.g., text message and/or email), or any combination thereof. The one or more network modules may receive data and/or information from the one or more user interfaces, relay data and/or information to the one or more user interfaces, received data and/or information from one or more networks, relay data to one or more networks, or any combination thereof. The one or more networks may include a medical network.

The treatment management system may include a monitoring module. The monitoring module may function to connect a patient with one or more caregivers, trusted contacts, physicians, or any combination thereof.

The monitoring module may be a framework by which patient data may be provided by one or more caregivers. For example, where the patient is a child, the caregiver of the child may provide patient data to the treatment management system if the child is not mature enough to be relied upon to make complete and regular data entries. The caregivers may supplement patient data entries provided by the one or more patients. For example, the caregiver may be a parent who prepares meals for their household and so the caregiver may provide food journal data related to family meals.

The monitoring module may include a framework by which one or more patients may be monitored by one or more caregivers, trusted contacts, or both. The patients may be monitored for a period after dosing with a medication. The patients may be monitored in case they have an adverse reaction to medication and need medical assistance. For example, medication used in food allergy immunotherapy may cause anaphylaxis, which first requires one or more injections of epinephrine and immediately thereafter emergency medicine care at a hospital.

The one or more patients may be actively or passively monitored. Active monitoring may mean that the one or more patients is physically proximal, in the immediate vicinity of, or visually observed by the one or more caregivers, trusted contacts, or both. Active monitoring may be performed by physical presence of an individual proximal to a patient, a virtual video connection, or both. That is, the patient may be viewable by caregivers and/or trusted contacts via a digital video. Passive monitoring may mean that one or more caregivers, trusted contacts, or both are on stand-by to engage in active monitoring or otherwise respond to an emergency of the patients. That is, the caregivers and/or trusted contacts may be notified that a patient has taken a dose of medication. The caregivers and/or trusted contacts may be reminded to check-in with the patient once or periodically.

Active monitoring may be particularly advantageous for a period of time immediately after dosing with a medication, when the risks of an adverse reaction are particularly acute. Active monitoring via a virtual video connection may be particularly advantageous in the event the patient is away from home, the patient is remote from the one or more caregivers or one or more trusted contacts, or both. For example, if the patient is on vacation, a caregiver can monitor the patient via a virtual video connection. Passive monitoring may be particularly advantageous for a period of time after the risks of an adverse reaction are no longer acute.

The monitoring module may comprise one or more devices and networks. The monitoring module may comprise one or more patient devices, physician devices, pharmacist devices, or any combination thereof. The devices may include one or more user interfaces, network modules, or both. The user interfaces may receive data, relay data, or both. The user interfaces may enable the parties to communicate with each other. The parties may communicate visually, audibly, textually, or any combination thereof. The network modules may receive data from the one or more user interfaces, relay data to the one or more user interfaces, received data from one or more networks, relay data to one or more networks, or any combination thereof. The one or more networks may be a personal network.

The treatment management system may include a medical information module. The medical information module may function to exchange and/or store patient data. The patient data may originate from one or more caregivers, patients, physicians, pharmacists, insurance providers, clinical laboratories, or any combination thereof.

The medical information module may include one or more databases, networks, devices, or any combination thereof. The databases may receive patient data, relay patient data, apply algorithms to patient data, perform one or more rules (i.e., "protocols") on patient data, or any combination thereof. The networks may include one or more medical networks, personal networks, or both. The devices may include one or more patient devices, caregiver devices, trusted contact devices, physician devices, pharmacist devices, insurance provider devices, clinical laboratory devices, or any combination thereof.

The treatment management system may include one or more networks. The networks may function to connect and/or transmit data between one or more devices, databases, memory storage media, processors, or any combination thereof. The devices may be in selective communication with the networks. The networks may be formed by placing two or more devices in communication with one another. One or more networks may be connected to one or more other networks.

The networks may include one or more local area networks ("LAN"), wide area networks ("WAN"), virtual private networks ("VPN"), intranet, Internet, the like, or any combination thereof. A VPN may be particularly advantageous for the transmission of any data subject to the Health Insurance Portability and Accountability Act ("HIPAA") and/or any other foreign analogues. The networks may include a cellular network, which may comprise a distributed network of cells, each including a transceiver. The networks may include a wireless network. The wireless network may include a Wi-Fi network.

The networks may be temporarily, semi-permanently, or permanently connected to one or more devices, or any combination thereof. The networks may allow for one or more devices to be connected to one or more other devices to transmit data signals, receive data signals, or both. The networks may provide for one or more signals from one or more controllers to be relayed through the system to one or more other controllers, devices, processors, memory storage media, the like, or any combination thereof. The networks may allow for one or more devices to receive one or more data entries from and/or transmit one or more data entries to one or more memory storage media. The networks may allow for transmission of one or more signals, status signals, data entries, instruction signals, or any combination thereof, for processing by one or more processors.

The networks may include one or more medical networks, personal networks, back-end networks, or any combination thereof. The medical networks may connect one or more patient devices with one or more medical entity devices. The medical entity devices may include one or more physician devices, pharmacist devices, insurance provider devices, clinical laboratory devices, or any combination thereof. The personal networks may connect one or more patient devices with one or more caregiver devices, trusted contact devices, or both. The back-end networks may connect one or more application provider devices with one or more third-party application provider devices and/or independent data source devices.

The treatment management system may include one or more firewalls. The one or more firewalls may function to protect devices from malware by inspecting data sent to the devices via a network to determine whether the data packet is dangerous. The one or more firewalls may comprise software, hardware, or both. The one or more firewalls may include packet-filtering firewalls, circuit-level gateways, stateful inspection firewalls, application-level gateways (a.k.a. proxy firewalls), next-gen firewalls, or any combination thereof. The one or more firewalls may be employed by a patient device, a physician device, a pharmacist device, a caregiver device, a trusted contact device, an insurance provider device, a clinical laboratory device, an application provider device, a third-party application provider device, a pharmaceutical company device, an independent data source device, a cloud-based device, or any combination thereof.

The treatment management system may include one or more devices. The devices may function to receive and/or transmit one or more signals, convert one or more signals to data entries, send one or more data entries to one or more memory storage media, retrieve one or more data entries from one or more memory storage media, execute one or more computer-executable instructions, compute one or more algorithms, apply one or more rules (i.e., "protocol"), or any combination thereof. The devices may include or be in communication with one or more other devices, processors, memory storage media, databases, user interfaces, or any combination thereof.

The devices may communicate with one or more other devices, processors, memory storage media, databases, or any combination thereof via an interaction interface. The interaction interface may include an application programming interface ("API").

The device may include one or more personal computers, mobile devices, or both. The personal computers may be laptop computers, desktop computers, or both. The mobile devices may be tablets, mobile phones, smart watches, the like, or any combination thereof. The devices may include patient devices, physician devices, pharmacist devices, caregiver devices, trusted contact devices, or any combination thereof. The patient device may be owned and/or used by the patient. The physician device may be owned and/or used by the physician, the pharmacist device may be owned and/or used by the pharmacist, the caregiver device may be owned and/or used by the caregiver, and the trusted contact device may be owned and/or used by the trusted contact.

The treatment management system may include one or more diagnostic devices. The diagnostic devices may function to obtain vital signs from the one or more patients, receive biological samples from the one or more patients, process the biological samples, output biomarker data from the biological samples, or any combination thereof. The diagnostic devices may collect patient data.

The diagnostic devices may be in communication with one or more devices (e.g., a patient device). The diagnostic devices may communicate with one or more devices via one or more networks. For example, the diagnostic devices may collect vital signs and transmit the vital signs to a device via Bluetooth®.

The diagnostic devices may include commercially available devices or clinical devices. Commercially available devices may include smart watches, activity monitors (e.g., step counter), heart rate monitors, blood pressure monitors, thermometers, glucose monitors, the like, or any combination thereof. An example of a suitable commercially available diagnostic device is the Apple Watch, commercially available from Apple, Inc. Clinical devices may include hematology analyzers, blood gas analyzers, chemical analyzers, histology equipment, cytology equipment, urinalysis analyzers, DNA analyzers, the like, or any combination thereof.

The treatment management system may include one or more medication devices. The medication devices may function to store medication, deliver medication to a patient, transmit medication journal data, or any combination thereof. The medication devices may include pill bottles, syringes, injectors, containers, the like, or any combination thereof. The injector may include an epinephrine auto injector ("EAI"). The medication devices may include Internet of Medical Technology ("IoMT") devices. An example of a suitable medication device may include the Pillsy medication packaging, commercially available from Pillsy, Inc. An example of a suitable medication device is described in U.S. Application No. 2019/0366001 A1, incorporated herein by reference in its entirety for all purposes.

The medication devices may receive data, transmit data, or both. The medication devices may include one or more network modules. The medication devices may communicate with one or more devices, networks, databases, memory storage media, processors, or any combination thereof via the one or more network modules. The medication devices may collect data, generate data, or both. The medication devices may collect data and/or generate data associated with the use of medication. The data may indicate if a medication is used, when a medication is used, a quantity of medication used, location of the medication, a temperature of the medication, an expiration date of the medication, the like, or any combination thereof.

The one or more devices may include one or more processors. The processors may function to analyze one or more signals from one or more applications, memory storage media, databases, network modules, or any combination thereof. The processors may be located within and/or in communication with one or more devices, servers, memory storage media, or any combination thereof. One or more processors may be in communication with one or more other processors. The processors may function to execute part or all of one or more applications, process data, execute one or more algorithms to analyze data, apply one or more rules (i.e., "protocol"), evaluate data against one or more rules, or any combination thereof. Processing data may include receiving, transforming, outputting, executing, the like, or any combination thereof. Examples of suitable processors may include the Apple A13 Bionic or the ARM® Cortex®-M4 32-bit processor with FPU, incorporated herein by reference in its entirety for all purposes.

The processors may be part of hardware, software, or both. The one or more hardware processors may include one or more central processing units ("CPU"), multi-core processors, front-end processors, the like, or any combination thereof. One or more software processors may include one or more word processors, document processors, the like, or any combination thereof. One or more system processors may include one or more information processors, the like, or any combination thereof.

The processors may be located within a same or different device as one or more memory storage media, other processors, network modules, or any combination thereof. The processors may include one or more cloud-based processors. A cloud-based processor may be part of or in communication with a dispatch interface, an interaction interface, or both. A cloud-based processor may be located remote from one or more computing devices, other processors, databases, or any combination thereof. Cloud-based may mean that the one or more processors may reside in a non-transitory memory storage medium located remote from a computing device, other processor, one or more databases, or any combination thereof. One or more cloud-based processors may be accessible via one or more networks. An example of a suitable cloud-based processor may be Amazon Elastic Compute Cloud™ (EC2™), provided by Amazon Web Services®, incorporated herein by reference in its entirety for all purposes. Another suitable exemplary platform for a cloud-based processor may include Lambda™ provided by Amazon Web Services®, incorporated herein by reference in its entirety for all purposes.

The processors may convert data signals to data entries to be saved within one or more memory storage media. The processors may utilize one or more algorithms to analyze one or more data entries and/or data signals. The processors may access one or more algorithms saved within one or more memory storage media.

The one or more devices may include one or more memory storage media ("computer-readable storage media"). The memory storage media may function to store one or more applications, data, databases, algorithms, rules, computer-executable instructions, the like, or any combination thereof. The memory storage media may function to cooperate with one or more processors for accessing, executing, and/or storing one or more applications, data, databases, algorithms, rules, computer-executable instructions, the like, or any combination thereof.

The memory storage media may be solid state disk ("SSD") or hard drive disk ("HDD"). The memory storage media may include one or more hard drives (e.g., hard drive memory), chips (e.g., Random Access Memory "RAM"), discs, flash drives, memory cards, the like, or any combination thereof. One or more discs may include one or more floppy diskettes, hard disk drives, optical data storage media, the like, or any combination thereof. The optical data storage media may include CD ROMs, DVDs, the like, or any combination thereof. One or more chips may include ROMs, flash RAM, EPROMs, hardwired or preprogrammed chips, nanotechnology memory, the like, or any combination thereof.

The memory storage media may include one or more cloud-based memory storage media. Cloud-based may mean that the one or more memory storage media may reside in a non-transitory memory storage medium located remote from the one or more computing devices. One or more cloud-based memory storage media may be accessible via one or more networks. A suitable cloud-based memory storage media may be Amazon S3™ provided by Amazon Web Services®, incorporated herein by reference in its entirety for all purposes.

The data stored within one or more memory storage media may be compressed, encrypted, or both. The memory storage media may store one or more data entries in a native format, foreign format, or both. The memory storage media may store data entries as objects, files, blocks, or any combination thereof. The memory storage media may be located within, part of, or in communication with one or more devices, processors, user interfaces, the like, or any combination thereof. The memory storage media may include one or more applications, algorithms, rules, databases, data entries, the like, or any combination thereof stored therein. The memory storage media may store data in the form of one or more databases.

The treatment management system may include one or more databases. The databases may function to receive one or more data entries, store one or more data entries, allow for retrieval of one or more data entries, or any combination thereof. The databases may be stored on one or more memory storage media.

The databases may include any type of database able to store digital information. The digital information may be stored within one or more databases in any suitable form using any suitable database management system ("DBMS"). Exemplary storage forms may include but are not limited to relational databases, non-relational databases, correlation databases, ordered/unordered flat files, structured files, the like, or any combination thereof. The relational databases may include SQL database, row-oriented, column-oriented, or any combination thereof. The non-relational databases may include NoSQL database. The databases may store one or more classifications of data models. The classifications may include column (e.g., wide column), document, key-value (e.g., key-value cache, key-value store), object, graph, multi-model, or any combination thereof.

One or more databases may be located within or be part of hardware, software, or both. One or more databases may be stored on a same or different hardware as one or more other databases. The databases may be located within one or more non-transitory memory storage media. The databases may be located in a same or different non-transitory memory storage medium. The databases may be accessible by one or more processors to retrieve data entries for analysis via one or more algorithms. The databases may include one or more cloud-based databases. Cloud-based may mean that the one or more databases may reside in a non-transitory memory storage medium located remote from the one or more computing devices. One or more cloud-based databases may be accessible via one or more networks. The databases may be capable of storing patient data. A suitable database service may be Amazon DynamoDB® offered through Amazon Web Services®, incorporated herein by reference in its entirety for all purposes.

The databases may include one or more physician databases, pharmacy databases, insurance provider databases, clinical laboratory databases, application provider databases, or any combination thereof.

The one or more databases may be HIPPA compliant. HIPPA compliant may mean that the database includes and/or is associated with any combination of the following features: complete data encryption, encryption key management, unique user identifications, user authentication, user authorization, audit logs, database backups, dedicated infrastructure, HIPPA-trained support personnel, regular automatic updates, data disposal methods, and business associate agreements.

The one or more devices may include one or more user interfaces. The user interfaces may function to display information, receive user inputs, transmit information, or any combination thereof. The user interfaces may be located on a device (e.g., a mobile phone screen), remote from s device (e.g., a monitor separate from a computer), or both. The user interfaces may relay information (e.g., data signals) to a user, receiving information (e.g., data entries) from a user, or both. The user interfaces may display information.

The user interfaces may include one or more cameras, graphical user interfaces ("GUI"), microphones, speakers, keyboards (e.g., physical keyboard, digital keyboard, or both), mice, touch pads, or any combination thereof.

The one or more user interfaces may include one or more cameras. The cameras may function to capture one or more videos, images, frames, the like, or any combination thereof. The cameras may be integrated into the one or more devices, remote from the one or more devices, or both. The cameras may have a wide-angle lens (e.g., viewing angle of 150 degrees or greater). The cameras may be capable of capturing static images, video recordings, or both at resolutions of about 480 pixels or greater, 640 pixels or greater, 720 pixels or greater, or even 1080 pixels or greater. The cameras may be able to capture video recordings at a frame rate of about 25 frames per second or greater, about 30 frames per second or greater, about 60 frames per second or greater, or even 90 frames per second or greater. An example of a suitable camera may be the camera integrated into the iPhone, commercially available from Apple, Inc., incorporated herein for all purposes.

The one or more user interfaces may include one or more graphical user interfaces ("GUI"). The graphical interfaces may include one or more screens. The screens may be located on the device (e.g., a mobile phone screen), remote from the device (e.g., a monitor separate from a computer), or both. The screens may be a screen on one or more personal computers, mobile devices (e.g., tablet, mobile phone, smart watch, etc.), or both.

The graphical user interfaces may be in communication with one or more user input devices. The user input devices may function to receive one or more inputs (i.e., "instruction signals") from a user. The input devices may include one or more buttons, wheels, keyboards, switches, mice, joysticks, touch pads (i.e., a touch-sensitive area, provided as a separate peripheral or integrated into a computing device, that does not display visual output), touch-sensitive screens, microphones, the like, or any combination thereof. The input devices may be integrated with the one or more graphical user interfaces. The touch-sensitive screens may function to accept input from a user based on tactile contact. The touch-sensitive screens may include a screen, a display controller, or both. The touch-sensitive screens may detect contact and convert the detected contact into interaction with one or more interface objects (e.g., buttons, icons, web pages, images, the like, or any combination thereof) that are displayed on the touch-sensitive monitor screen. The touch-sensitive screens may utilize liquid crystal display ("LCD") technology, light emitting polymer display ("LPD") technology, light emitting diode ("LED") technology, or organic light emitting diode (OLED) technology. The touch-sensitive screens may detect contact via touch sensing technology. The touch sensing technology may include capacitive, resistive, infrared, surface acoustic wave technologies, or any combination thereof. The touch-sensitive screens may detect contact from an appendage (e.g., finger), an object (e.g., a stylus), or both.

The one or more user interfaces may include microphones. The microphones may function to receive sound from a user. The microphones may convert human-audible sound waves to electrical signals. The microphones may be integrated into the one or more devices, remote from the one or more devices, or both. An example of a suitable microphone may be the microphone integrated into the iPhone, commercially available from Apple, Inc., incorporated herein for all purposes.

The one or more user interfaces may include one or more speakers. The speakers may function to project sound to a user. The speakers may convert electrical signal to human-audible sound waves. The speakers may be integrated into the one or more devices, remote from the one or more devices, or both. An example of a suitable speaker may be the speaker integrated into the iPhone, commercially available from Apple, Inc., incorporated herein for all purposes.

The one or more devices may include one or more network modules. The network modules may allow for the one or more devices to receive and/or transmit one or more signals from one or more devices, be integrated into a network, or both.

The network modules may include one or more wired network modules, wireless network modules, or both.

A wired network module may be any module capable of transmitting and/or receiving one or more data signals via a wired connection. The wired network module may communicate via one or more networks via a direct, wired connection. A wired connection may include a local area network ("LAN") wired connection by an ethernet port. A wired network module may include a PC Card, PCMCIA card, PCI card, the like, or any combination thereof.

A wireless network module may include any module capable of transmitting and/or receiving one or more data signals via a wireless connection (e.g., cellular network, Bluetooth®, Wi-Fi, the like, or any combination thereof). The wireless network modules may communicate via one or more networks via a wireless connection. The wireless network modules may include a Wi-Fi transmitter, a Bluetooth® transmitter, an infrared transmitter, a radio frequency transmitter, an IEEE 802.15.4 compliant transmitter, a GNSS module, and NFC module, the like, or any combination thereof. A Wi-Fi transmitter may be any transmitter complaint with IEEE 802.11. A wireless network module may be single band, multi-band (e.g., dual band), or both. A wireless network module may operate at 2.4 Ghz, 5 Ghz, the like, or any combination thereof.

The network modules may communicate with one or more other network modules, devices, processors, or any combination thereof directly via one or more networks.

The one or more devices may include one or more location modules. The location modules may function to send and/or receive location information from a global positioning system ("GPS") satellite. The location information may be defined by latitude, longitude, altitude, or any combination thereof. Relating the latitude, longitude, altitude, or any combination thereof, of one location to another location may denote movement information (e.g., distance, speed, or both).

C. Data Collection

The system and method of the present disclosure may utilize one or more data entries. The data entries may comprise patient data. The patient data may be used to monitor treatment, assist physicians issue medical guidelines, assist pharmacists issue medication guidelines, inform insurance providers of treatment compliance, provide medical researchers with a data pool to conduct treatment studies, provide the patient with an indication of treatment progress and/or efficacy, or any combination thereof. The patient data may be obtained from patients using the treatment management system of the present disclosure.

The patient data may be obtained from and/or input into the treatment management system by one or more input sources. The one or more input sources may include one or more human inputs, machine inputs, or both. The human inputs may include data input by a human via a user interface. For example, a human may input data via a keyboard. The machine inputs may include data obtained from and/or input into the treatment management system by one or more devices, diagnostic devices, medication devices, processors, memory storage media, databases, or any combination thereof. For example, a heart rate monitor may input heart rate data. As another example, a medication device may input medication data. The patient data may be input into the treatment management system manually or autonomously. Manual input may mean data is input by a human via a user interface. Autonomous input may mean data is obtained electronically from an input source and/or input into the treatment management system without the need for a human to interact with a user interface. For example, a patient's heart rate may be collected by a wearable heart rate monitor and autonomously obtained from the wearable heart rate monitor and input into the treatment management system without a patient interacting with their device. As another example, a patient's calendar data may be autonomously obtained from a third-party calendar application and input into the treatment management system. The autonomous input may be particularly advantageous in promoting use of the application of the present disclosure by relieving the patient from the time-consuming task of manually inputting data for a multiplicity of data types and perhaps multiple times in a day.

The patient data may be manually input into the treatment management system via one or more patient devices, caregiver devices, physician devices, pharmacist devices, or any combination thereof. The patient data may be autonomously input into the treatment system via one or more diagnostic devices, medication devices, third-party applications, or any combination thereof. The third-party applications may include calendar applications, text message applications, phonebook applications, phone applications, email applications, recipe applications, 2D code scanner applications, location services applications, the like, or any combination thereof.

The treatment management system may retrieve data from a third-party application via an interaction interface (e.g., application programming interface ("API")). One or more third-party applications, insurance providers, pharmacies, physicians, clinical laboratories, pharmaceutical companies, or any combination thereof may view and/or retrieve data from the treatment management system via an API. Information exchange via an API may be protected by an encryption protocol. The encryption protocol may include Transport Layer Security (TLS), Secure Sockets Layer (SSL), IP security (IPSec), secure shell (SSH), Pretty Good Privacy (PGP), the like, or any combination thereof.

The patient data may be input in real-time. The patient data may be input upon a patient initiating syncing of a patient device. The patient device may sync with one or more diagnostic devices, medication devices, remote databases, or any combination thereof.

The patient data may include profile data, biomarker data, vital sign data, quality of life data, food journal data, medication journal data, medical guidelines data, reaction data, calendar data, or any combination thereof. The patient data may be stored on the patient device or remote from the patient device. The patient data may be stored in a memory storage medium integrated in the patient device. The patient data may be stored in a cloud-based memory storage device that is remote from the patient device. The patient data may be stored in a database.

The patient data may include profile data. The profile data may include any suitable data identifying patients and general characteristics of the patients. The profile data may include name, age, weight, height, allergen, allergy severity, or any combination thereof. The profile data may be manually input into the treatment management system. The profile data may be input into the treatment management system by one or more patients, caregivers, physicians, or any combination thereof.

The patient data may include biomarker data. The biomarker data may be associated with pathological testing performed on the patient. The biomarker data may be manually input, autonomously input, or both into the treatment management system. The biomarker data may be manually input by one or more patients, caregivers, physicians, clinical laboratories, or any combination thereof. The biomarker data may be autonomously input into the treatment management system by one or more diagnostic devices. The biomarker data may include blood histamine concentration, urine histamine concentration, antibodies, the like, or any combination thereof.

The patient data may include vital sign data. The vital sign data may be obtained by diagnostic devices. The vital sign data may be manually input, autonomously input, or both into the treatment management system. The vital sign data may be manually input into the treatment management system by one or more patients, caregivers, physicians, or any combination thereof. The vital sign data may be autonomously input into the treatment management system by one or more diagnostic devices. The vital sign data may include heart rate, pulse rate, respiration rate, blood pressure, body temperature, the like, or any combination thereof.

The patient data may include quality of life ("QOL") data. The quality of life data may be associated with quality of life entries by the patient. The quality of life data may be manually input into the treatment management system. The quality of life data may be manually input into the treatment management system by one or more patients, caregivers, or both.

The quality of life data may include quality of life metrics, associations, dates, or any combination thereof. The quality of life metric may include a measure of emotion, satisfaction, or both. The emotion may include an emotion associated with the treatment. For example, a patient may express that they are psychologically stressed as a result of the treatment. The satisfaction may include a level of satisfaction associated with the treatment. For example, a patient may express they are satisfied with how the treatment is progressing. The quality of life metric may be measured on a quantitative scale (e.g., a scale of 1 to 5). The quality of life metric may have an association with the treatment. The association may be directed to the treatment generally, to a particular portion of the treatment, or both. The particular portion of treatment may include progressive stages of increasing dosage quantities. Each of the progressive stages may have a duration of 1-week or more, 2-weeks or more, 1-month or more, or even 3-months or more. The association may include adverse reactions, schedule, treatment progress, the like, or any combination thereof. For example, a patient may express dissatisfaction with the frequency of adverse reactions. As another example, a patient may express satisfaction with the progress of treatment.

The quality of life data may be input multiple times per day, once per day, weekly, bi-weekly, any interval therebetween, or any combination thereof. The frequency of collection may vary over time. The quality of life data may indicate trends in quality of life as time progresses. The quality of life data may indicate trends in quality of life in relation to particular portions of treatment.

The patient data may include food journal data. The food journal data may be associated with meals consumed by the patient. The food journal data may be manually input, autonomously input, or both into the treatment management system.

The food journal data may be manually input into the treatment management system by one or more patients, caregivers, or both. The food journal data may be autonomously input into the treatment management system by one or more third-party applications. The one or more third-party applications may include recipe publishers, 2D code scanners, or both. Recipe publishers may provide recipes, nutritional information, serving sizes, ingredients, allergen information, or any combination thereof. An example of a suitable recipe publisher may include allergicliving.com, incorporated by reference herein for all purposes. 2D code scanners may scan 2D codes on the packaging of commercial products and obtain information associated with the 2D code. A 2D code may include barcodes, QR codes, data matrices, the like, or any combination thereof. The 2D code scanner may obtain information from other third-party applications via an interaction interface.

The food journal data may include food, date, time, location, consumer, serving size, food category, or any combination thereof. The food journal data may be input multiple times per day, once per day, weekly, bi-weekly, any interval therebetween, or any combination thereof. The time may be expressed numerically or colloquially (e.g., breakfast, lunch dinner, snack). The consumer may be the patient and anyone dining with the patient (e.g., family, friends). The food category may include risk food or neutral food. A risk food may contain one or more allergens. A neutral food may be free of allergens.

The patient data may include medication journal data. The medication journal data may be associated with instances medication dosing by the patient. The medication journal data may be input into the treatment management system manually, autonomously, or both. The medication journal data may be input into the treatment management system manually by one or more patients, caregivers, or both. The medication journal data may be autonomously input into the treatment management system by one or more medication devices. The medication journal data may include date, dose time, or both. The medication journal data may be input multiple times per day, once per day, weekly, bi-weekly, any interval therebetween, or any combination thereof.

The patient data may include medical guidelines data. The medical guidelines data may be associated with the medical guidelines provided by one or more physicians, pharmacists, or both. The medical guidelines data may be manually input into the treatment management system. The medical guidelines data may be manually input into the treatment management system by one or more physicians, pharmacists, or both. The medical guidelines data may be updated as treatment progresses. For example, a physician may suggest a 5-mg dose of medication at the outset of treatment and incrementally increase the dosage suggestion to 15-mg. The medical guidelines data may be updated after patient checkups by one or more physicians. The medical guidelines data may include medication, dose quantity, dose frequency, check-up frequency, monitoring period, refill date, expiration date, or any combination thereof.

The medical guidelines may be formulated by pharmaceutical companies, physicians, or both. The medical guidelines provided by pharmaceutical companies may be standard guidelines provided to prescribing physicians. The medical guidelines may be customized by physicians. The physicians may employ the system and method of the present disclosure to evaluate the efficacy of modifications to standard guidelines provided by pharmaceutical companies. The pharmaceutical companies may employ the system and method of the present disclosure to obtain information from physicians for use to modify previously established standard guidelines.

The patient data may include reaction data. The reaction data may be associated with instances of allergic reactions of the patient. The reaction data may be input into the treatment management system manually, autonomously, or both. The reaction data may be manually input into the treatment management system by one or more patients, caregivers, or both. The reaction data may be autonomously input into the treatment management system by a medication device. For example, an epinephrine auto injector ("EAI") having IoMT capabilities may autonomously input reaction data after the EAI is used by a patient. The reaction journal data may be input into the treatment management system after an adverse reaction. The reaction data may include reaction entry, date, time, symptoms, duration of symptoms, severity of symptoms, reaction medication, reaction medication quantity, or any combination thereof.

The patient data may include calendar data. The calendar data may be associated with calendar entries by the patient. The calendar data may be input into the treatment management system manually, autonomously, or both. The calendar data may be manually input into the treatment management system by one or more patients, caregivers, or both. The calendar data may be manually input into the treatment management system by one or more third-party applications. The calendar data may be autonomously input into the treatment management system by a calendar application. The calendar data may be input multiple times per day, once per day, weekly, bi-weekly, any interval therebetween, or any combination thereof.

The calendar data may include a name of the event, event time period, interim time period, category, or any combination thereof. The interim period may be a period of time between scheduled events. The category may include free time, controlled event, risk event, occupied event. Free time may indicate that no event is scheduled. Controlled event may indicate an event taking place in a controlled environment. The controlled environment may be at home, at work, at a friend's home, at a relative's home, or any combination thereof. For example, a family dinner at home may be a controlled event. A risk event may indicate an event that risks encouraging and/or exacerbating an adverse reaction. Risk events may include exercise, stress, activity that could increase body temperature (e.g., hot showers, sauna use, and the like), non-steroidal anti-inflammatory drug use, the like, or any combination thereof. Exercise, stress, activity that could increase body temperature, and non-steroidal anti-inflammatory drug use have been found to encourage and/or exacerbate adverse reactions resulting from food allergies. These should be avoided for at least 3-hours after dosing.

The patient data may include location data. The location data may be associated with the location of a patient and/or location-based reminders. The location data may be input into the treatment management system manually, autonomously, or both. The location data may be input into the treatment management system manually by one or more patients, caregivers, or both. The location data may be autonomously retrieved from one or more location modules and input into the treatment management system.

The location data may include a patient's current location, one or more saved locations, one or more geo-fences, or any combination thereof. The current location may be utilized in the event of an emergency. The current location may allow one or more caregivers, trusted contacts, emergency services, or any combination thereof locate the patient in the event the patient is undergoing an adverse reaction. The saved locations may be locations a patient normally frequents. The one or more saved locations may include the patient's home, the patient's work, homes of the patient's family, homes of the patient's friends, vacation homes, the like, or any combination thereof. The one or more geo-fences may be a virtual perimeter associated with a location, via GPS coordinates, and a radius. The one or more geo-fences may be associated with one or more reminders. For example, a patient crossing a geo-fence drawn around their home may remind the patient to bring an epinephrine auto injector with them.

One or more algorithms, one or more rules (i.e., "protocols"), or both may be applied to patient data to produce derivative data. The derivative data may function to summarize patient data, provide insight into the medical therapy of a patient, monitor the progress of the medical therapy of a patient, characterize the efficacy of the medication, characterize the efficacy of the application of the present disclosure, produce and/or alter medical guidelines, or any combination thereof. The one or more algorithms, the one or more rules, or both may be constructed by humans, constructed and/or improved by machine learning, or both. The one or more algorithms, one or more rules, or both may be standardized so that divergent calculation methods are not employed by different parties.

The derivative data may obviate the human error of analyzing raw patient data. For example, the derivative data may include medication efficacy as a function of dose quantity over time and adverse reactions over time, which may be provided to a physician upon request so that the physician does not have to filter through and analyze the raw patient data themselves. The derivative data may reduce the time and/or resources that would otherwise be used to analyze raw patient data.

The derivative data may be presented as one or more values, in tabular format, in chart format, or any combination thereof. The chart format may include column chart, line chart, pie chart, doughnut chart, bar chart, area chart, XY (scatter) chart, bubble chart, the like, or any combination thereof.

The derivative data may be provided to one or more patients, one or more caregivers, one or more physicians, one or more pharmacists, one or more insurance providers, one or more clinical laboratories, one or more application providers, one or more pharmaceutical companies, or any combination thereof. The derivative data may be produced by one or more processors.

The one or more processors may apply one or more algorithms, one or more rules, or both to patient data and output derivative data. The one or more processors may be associated with one or more patient devices, one or more physician devices, one or more pharmacist devices, one or more insurance provider devices, one or more clinical laboratory devices, one or more application provider devices, one or more pharmaceutical companies, a cloud-based device, or any combination thereof.

The derivative data may be produced in substantially real-time, periodically, upon request, or any combination thereof. The derivative data may be produced in substantially real-time upon the receipt of new and/or updated patient data. The derivative data may be produced periodically on an hourly basis, on a daily basis, on a weekly basis, on a monthly basis, or any combination thereof. The derivative data may be produced on request by one or more patients, one or more caregivers, one or more physicians, one or more pharmacists, one or more insurance providers, one or more clinical laboratories, one or more application providers, one or more pharmaceutical companies, or any combination thereof.

D. Software and Method

The method may comprise one or more of the following steps. Some of the steps may be duplicated, removed, rearranged relative to other steps, combined into one or more steps, separated into two or more steps, or any combination thereof.

The methods described hereunder may be carried out by a patient device and/or or a cloud-based device remote from the patient device. The cloud-based device may perform cloud computing. At least a portion of the method may be performed by the patient device, at least a portion of the method may be performed by a remote device (e.g., a server), or both.

The method may be embodied by computer executable instructions stored on one or more memory storage media and or executed by a processor of the patient device and/or remote device. The method may be stored, as computer executable instructions, by one or more memory storage media of the patient device and/or the remote device. Patient data utilized by the method may be stored by one or more memory storage media of a patient device and/or a remote device.

The method, being embodied by computer executable instructions, may be performed by a processor. The processor may be of the patient device and/or remote device. The method may be initiated by a processor. The method may be initiated manually and/or automatically. Manual initiation may mean initiation upon receiving an instruction from the patient. Automatic initiation may mean initiation upon the occurrence of a trigger. The method may be automatically initiated by a processer receiving a signal from a trigger. The trigger may include receiving a signal from a medication device; receiving a signal from a diagnostic device; receiving a patient data input from a patient, one or more caregivers, one or more physicians, one or more pharmacists, or any combination thereof; receiving a signal from a GPS module; or any combination thereof.

The present disclosure provides for a method for suggesting a dosing time. The method for suggesting a dosing time may aid one or more patients in determining ideal dosing times. Immunotherapy for food allergies imposes certain restrictions on patients. Patients are recommended to undergo a monitoring period of 1 to 4 hours after dosing. The monitoring period may be a period of time whereby the risks of an adverse reaction are elevated. During the monitoring period it is clinically suggested that patients forego exercise, stressful activity, activity that would raise body temperature, ingestion of non-steroidal anti-inflammatory drugs, or any combination thereof. During the monitoring period or at least a portion thereof, it is suggested that patients be virtually monitored and/or in the immediate vicinity of one or more caregivers, trusted contacts, or both. During the monitoring period it is important that patients have access to support in the event the patient suffers an adverse reaction. Thus, the present disclosure provides for a method that assists patients maintain consistent dosing schedules while minimizing the impact of medication dosing on day-to-day life.

The present disclosure provides for a method for suggesting a dosing time based upon an interim period between events. The patient device and/or remote device may receive, manually and/or automatically, calendar data including events, event time periods, interim time periods, categories, or any combination thereof. One or more processors of the patient device and/or remote device may receive, manually and/or automatically, calendar data including events, event time periods, interim time periods, categories, or any combination thereof. One or more processors of the patient device and/or remote device may initiate and/or perform the method upon receiving, manually and/or automatically, calendar data including events, event time periods, interim time periods, categories, or any combination thereof. The patient device and/or remote device may categorize events using artificial intelligence if the categories are not already provided. The patient device and/or remote device may receive, manually and/or automatically, a monitoring period. The monitoring period may be a period of time, the duration of which is suggested by a physician, during which certain lifestyle restrictions are imposed on patients. The patient device and/or remote device may consider the first two events in a daily calendar. The patient device and/or remote device may compare the monitoring period to the interim time period between a first event and a second event. If the monitoring time period is greater than the interim time period, then subsequent events are considered in chronological order (e.g., second event and third event, and so on) and the comparing step is repeated. If the monitoring time period is less than or equal to the interim time period, then a dosing time is generated. The dosing time may be a suggested time a patient doses with a medication.

The method may include a step of determining if a first event and/or a second event is a risk event. If the first event and/or the second event is a risk event, then subsequent events are considered in chronological order (e.g., second event and third event, and so on) and the comparing step is repeated. That is, in order to avoid dosing in proximity to a risk event, interim time periods that are proximate to risk events may be disregarded for dosing times, unless the interim time period occupies the entirety of the monitoring period. For example, a patient's calendar may be free of any appointments for an hour prior to a sporting event the patient is participating in. While the time of dosing is one hour prior to the sporting event, a dosing time will not be generated for the beginning of this interim period because the patient may be recommended not to engage in physical activity for two hours after dosing.

The present disclosure provides for a method for suggesting a dosing time based upon a controlled event. A controlled event may be an event in a controlled environment (e.g., at a patient's home). A patient may choose to dose during a controlled event because risks are minimized in a controlled environment. By way of comparison, a non-limiting example of an uncontrolled environment may be in a vehicle while the patient is transiting to work. The method for suggesting a dosing time based upon a controlled event may be performed synchronous with or in the alternative to the method for suggesting a dosing time based upon an interim period between events. The patient device and/or remote device may receive, manually and/or automatically, calendar data including events, event time periods, interim time periods, categories, or any combination thereof. One or more processors of the patient device and/or remote device may receive, manually and/or automatically, calendar data including events, event time periods, interim time periods, categories, or any combination thereof. One or more processors of the patient device and/or remote device may initiate and/or perform the method upon receiving, manually and/or automatically, calendar data including events, event time periods, interim time periods, categories, or any combination thereof. The patient device and/or remote device may categorize events using artificial intelligence if the categories are not already provided. The categories may be provided by a patient, one or more caregivers, or both. The patient device and/or remote device may receive, manually and/or automatically, a monitoring period. The monitoring period may be a period of time, suggested by a physician, during which certain lifestyle restrictions are imposed on patients. The patient device and/or remote device may consider the first two events in a daily calendar. The patient device and/or remote device may compare the monitoring period with the time period of a controlled event. If the monitoring period is greater than the time period of the controlled event then subsequent events are considered in chronological order (e.g., second event and third event, and so on) and the comparing step is repeated. If the monitoring period is less than or equal to the time period of the controlled event, then a dosing time is generated.

The present disclosure provides for a method for suggesting a dosing time based upon food journal data. Consuming allergen containing foods and/or foods known to promote inflammation may increase the chances of an adverse reaction during dosing. This risk is particularly acute if the dosing time and the time of food ingestion are proximate in time. A patient and/or remote device may receive, manually and/or automatically, food journal data. One or more processors of the patient device and/or remote device may receive, manually and/or automatically, food journal data. One or more processors of the patient device and/or remote device may initiate and/or perform the method upon receiving, manually and/or automatically, food journal data. The food journal data may include a food category. The food category may include a risk food or a neutral food. The patient and/or remote device may determine if a risk food has been consumed within a pre-determined time from the dosing time. If no risk food has been consumed within a pre-determined time from the dosing time, no adjustment to the dosing time occurs. If a risk food has been consumed within a pre-determined time from the dosing time, then a dosing time is evaluated for subsequent events in chronological order (e.g., second event and third event, and so on) according to either or both of the method for suggesting a dosing time based upon an interim time period between events and the method for suggesting a dosing time based upon a controlled event.

The present disclosure provides for a method of notifying one or more caregivers and/or trusted contacts that monitoring is desired. Once a dosing time is determined according to the methods described above, a patient may want to communicate the dosing time to one or more caregivers and/or one or more trusted contacts so that appropriate monitoring may be arranged. It may be desirable to communicate dosing times autonomously or semi-autonomously in order to alleviate the patient of the time and energy of arranging for monitoring otherwise (e.g., conducting phone calls, drafting text messages, and the like). After a dosing time is determined, a patient device may automatically inquire the patient whether monitoring is desired. If the patient indicates no monitoring is desired, then no monitoring is requested of caregivers and/or trusted contacts. If the patient indicates that monitoring is desired, then the patient device may generate a list of one or more caregivers and/or one or more trusted contacts. The patient device may receive a selection of one or more caregivers and/or one or more trusted contacts from the patient. If the patient indicates that monitoring is desired, then the patient device may autonomously send notifications to preselected caregivers and/or trusted contacts. The patient device may send notifications to the selected caregivers and/or trusted contacts.

The present disclosure provides for a method for a reaction response. In the event of an adverse reaction, the patient may use reaction medication. The reaction medication may include epinephrine delivered via an epinephrine auto injector. Additionally, the patient may desire to autonomously notify one or more trusted contacts, caregivers, emergency services (e.g., EMS, fire department, police department), or any combination thereof. Additionally, the patient may desire to inform bystanders of emergency instructions. The method may be initiated by a signal received from a medical device. The medical device may include an epinephrine auto injector equipped with IoMT technology. The patient device may receive a signal from a medication device indicating that the medication device is being or has been used. One or more processors of the patient device may receive, manually and/or automatically, a signal from a medication device. One or more processors of the patient device may initiate and/or perform the method upon receiving, manually and/or automatically, a signal from a medication device. The signal may be generated by a patient interacting with the patient device to generate a notification. The patient device may generate a communication. The communication may be transmitted, manually and/or automatically, to one or more trusted contacts, caregivers, emergency services, or any combination thereof. The patient device may manually and/or automatically unlock to provide access to bystanders. The patient device may manually and/or automatically display emergency instructions. The emergency instructions may be accessible to bystanders. The emergency instructions may function to inform bystanders how to react to the adverse reaction. The emergency instructions may include instructions on how to administer medication (e.g., epinephrine), how to administer first aid, to contact emergency services, where the nearest hospital is located, the like, or any combination thereof.

The present disclosure provides for a method of determining treatment adherence. Treatment adherence may refer to the consistency with which the patient uses the treatment management system of the present disclosure, adheres to treatment guidelines, or both. Treatment adherence may be indicated by an adherence parameter. The adherence parameter may be a function of food journal entries, medication entries, quality of life entries, or any combination thereof. The method may be performed at a pre-determined interval of time, by request of one or more patients, by request of one or more physicians, by request of one or more pharmacists, by request of one or more insurance providers, by request of one or more pharmaceutical companies, or any combination thereof. The pre-determined interval of time may be daily, weekly, monthly, yearly, or any interval therebetween. One or more processors of a patient device may initiate and/or perform the method automatically. One or more processors of a patient device may initiate and/or perform the method automatically upon occurrence of the pre-determined interval of time, upon receiving one or more requests from one or more patients, one or more physicians, one or more pharmacists, one or more insurance providers, one or more pharmaceutical companies, or any combination thereof. The patient device and/or remote device may obtain, manually and/or automatically, a total amount of food journal entries, medication entries, quality of life entries, or any combination thereof. The patient device and/or remote device may determine the total possible amount of food journal entries, medication entries, quality of life entries, or any combination thereof. The total possible amount of medication entries may be determined by treatment guidelines. For example, treatment guidelines may direct daily medication dosing. The total possible amount of food journal entries may be a pre-determined number of meals a patient typically consumes during a period of time. For example, a patient may typically consume three meals per day. The total possible amount of quality of life entries may be determined by the number of prompts for quality of life entries provided to patients and/or caregivers. For example, the system of the present disclosure may prompt patients once-per-day for a quality of life entry. The patient device and/or remote device may calculate an adherence parameter from the aforementioned data. The total possible number of entries may be a function of how long the treatment management system has been used by a patient and the suggested frequency of entries. For example, a patient may be suggested to take medication daily and the patient has used the treatment management system for 120 days; therefore, the total possible number of entries may be 120 days.

The present disclosure provides for a method of adjusting dosage. The patient may be advised to adjust dosage based upon the patient data. The adjustment may be an increase or a decrease. The adjustment may be related to one or more adjustment parameters. The one or more adjustment parameters may be a function of patient data. The one or more adjustment parameters may include an increased dosage quantity, a decreased dosage quantity, an increased dosage frequency, a decreased dosage frequency, or any combination thereof. The method may be performed at a pre-determined interval of time, by request of one or more patients, by request of one or more physicians, by request of one or more pharmacists, by request of one or more insurance providers, by request of one or more pharmaceutical companies, or any combination thereof. The pre-determined interval of time may be daily, weekly, monthly, yearly, or any interval therebetween. One or more processors of a patient device may initiate and/or perform the method automatically upon occurrence of the pre-determined interval of time, upon receiving a request from one or more patients, upon receiving a request from one or more physicians, upon receiving a request from one or more pharmacists, upon receiving a request from one or more insurance providers, upon receiving a request from one or more pharmaceutical companies, or any combination thereof. A patient device and/or remote device may receive, manually and/or automatically, a dose quantity. The patient device and/or remote device may receive, manually and/or automatically, one or more adjustment parameters. The patient device and/or remote device may calculate an adjusted dose based upon the dose quantity and the one or more adjustment parameters.

The present disclosure provides for a method for gamifying medical treatment. The method may include receiving, by a device, patient data. The method may include generating, by a device, a game feature based upon the patient data. The game feature may include challenges, levels, instant feedback, scores, badges, or any combination thereof. The method may include monitoring patient data associated with the game feature. The game feature may include a goal. The game feature may include a progress value. The progress value may comprise a comparison of the patient's current progress with a goal. The method may include comparing patient data with the goal of the game feature. The game feature may include challenges. The challenges may function to motivate a patient to reach a goal. The challenges may involve setting a goal and monitoring a patient's progress with respect to the goal. The challenges may include increasing the frequency of data entry by patients, increasing the volume of data entry by patients, increasing the regularity of a medication dosing schedule, scheduling regular appointments with a physician, avoiding allergen-containing foods, the like, or any combination thereof. The levels may function to indicate progress of the medical therapy. The levels may be proportional to the strength of a patient's immune system. The levels may comprise a single value on a scale of values. The levels may comprise numerical values, verbal values, or both. For example, the levels may be a numerical value on a scale of 1 to 100. As another example, the levels may be verbally conveyed as beginner, intermediate, professional, expert, the like, or any combination thereof. Individual levels may be associated with a patient's dose quantity. For example, a dose quantity recommended by a physician at the beginning of treatment may be associated with the lowest level and a dose quantity recommended by a physician after several years of medical therapy may be associated with an advanced level. The instant feedback may function to provide instant positive reinforcement to patients in response to entry of patient data. The instant feedback may comprise messages of affirmation, congratulatory messages, or both. The messages of affirmation may convey that the patient is performing well and/or progressing with respect to the medical therapy. The congratulatory messages may praise the patient for inputting data, reaching milestones, or both. The scores may function to rate a patient's performance with respect to one or more aspects of the treatment management system. The scores may be associated with one or more types of patient data. The scores may be associated with the frequency of patient data entry, the improvement of patient data as compared to patient data submitted prior in time, the comparison of a patient's data with patient data of other patients undergoing the same medical therapy, the like, or any combination thereof. The score may comprise a single value on a scale of values. The score may comprise numerical values, verbal values, or both. For example, the score may be a numerical value on a scale of 1 to 10. As another example, the score may be verbally conveyed as poor, fair, good, excellent, the like, or any combination thereof. The badges may function to reward patients for reaching a milestone. Each of the badges may include a visual design associated with a milestone. The milestone may include completion of a challenge, advancing levels, or both.

E. GUI

The treatment management system may include a graphical user interface ("GUI") displayed on the patient device, the caregiver device, or both. The GUI may function to receive inputs, display data, organize information, or any combination thereof. The GUI may concisely and neatly display data. The GUI may include an intuitive design. The GUI may be designed to streamline the interaction by the patient and/or caregiver with the device. The GUI may include a profile page, a food journal page, a medical guidelines page, a reaction journal page, a medication journal page, a quality of life journal page, or any combination thereof. The profile page may display and/or receive inputs of profile data. The food journal page may display and/or receive inputs of food journal data. The medical guidelines page may display and/or receive inputs of medical guidelines data. The reaction journal page may display and/or receive inputs of reaction journal data. The medication journal page may display and/or receive inputs of medication journal data. The quality of life page may display and/or receive inputs of quality of life journal data.

The graphical user interface may include one or more interface metaphors (i.e., "interface objects"). The interface metaphor may function to give the user instantaneous knowledge about how to interact with the user interface. The interface metaphor may include visuals, actions, and procedures that exploit specific knowledge that users may already possess from other domains of life. An example of an interface metaphor may be a file folder icon. A user generally intuitively knows a file folder icon contains one or more individual files. Another example of an interface metaphor may be one or more tabs in a window of a data processing program (e.g., Microsoft Excel), which a user intuitively knows to correspond with different pages. Another example of an interface metaphor may be a button displayed on a touch-sensitive monitor screen. A user generally intuitively knows that upon pressing a button, an associated function may be initiated.

The present disclosure provides for a physician portal. The physician portal may be accessible via a physician device. The physician portal may function to view and/or input patient data, view and/or input medical guidelines data, or both. The physician may manage one or more patients through the physician portal. The physician may select from one or more clinical standard guidelines for administering medications. The clinical standard guidelines may include a type of medication, a dosage quantity, a dosage frequency, foods the patient should avoid, other medications a patient should avoid, or any combination thereof. The clinical standard guidelines may be suggested by a pharmaceutical company producing, marketing, and selling the medication prescribed to a patient. The clinical standard guidelines may be modified by the physician. The physician may utilize patient data to modify clinical standard guidelines. For example, a physician may recommend to a patient who is progressing well in treatment to increase dosage frequency, surpassing clinical standard guidelines. The physician may evaluate treatment efficacy of a patient via the physician portal. The physician may view patient data, apply one or more analytical tools to patient data, or both.

DETAILED DESCRIPTION OF THE DRAWINGS

FIG. 1 is a schematic of a treatment management system 74. The treatment management system 74 includes a medical network 50, a personal network 52, and a back-end network 54.

Figure 2:
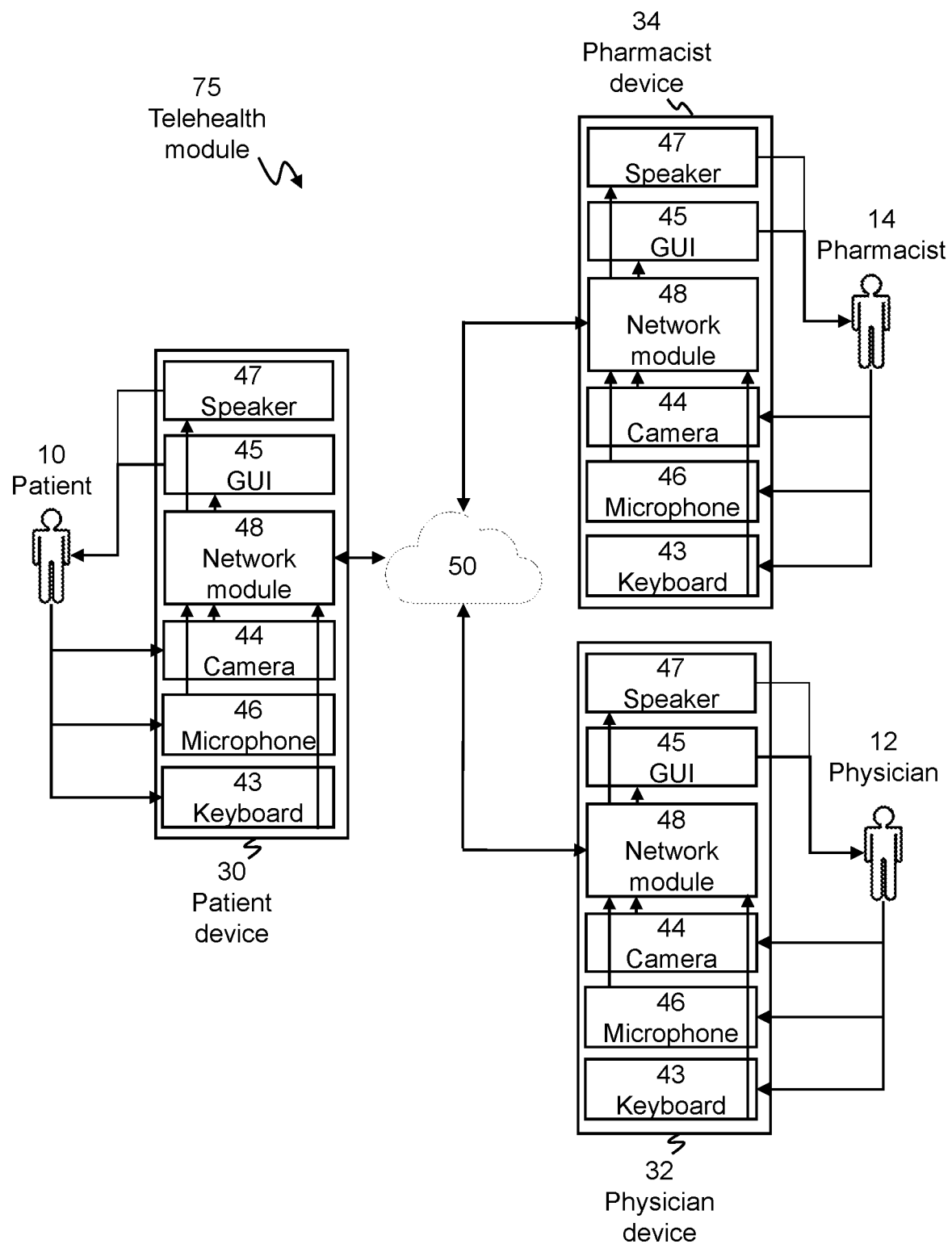
FIG. 2 is a schematic of a telehealth module.
Figure 5:
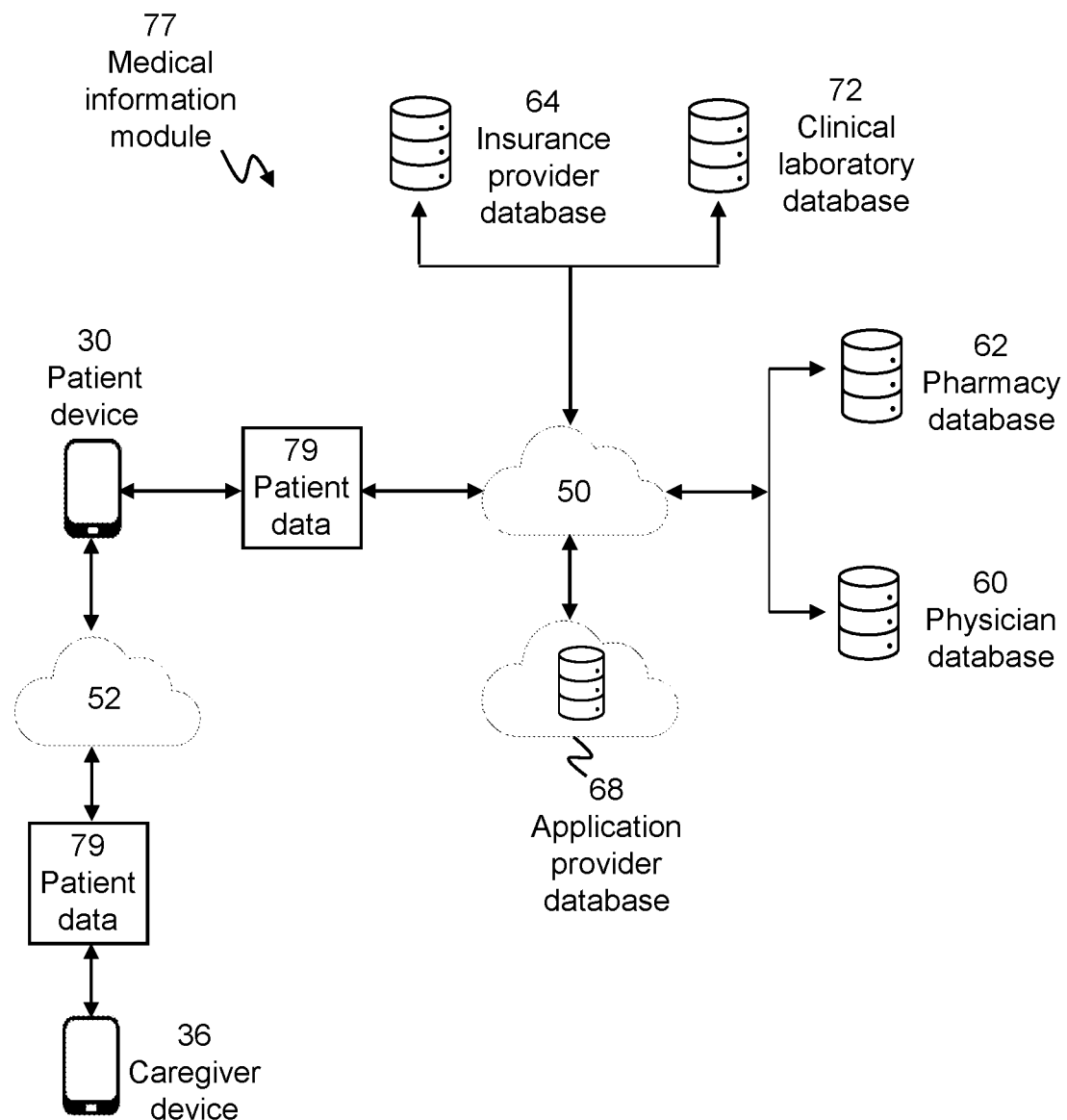
FIG. 5 is a schematic of a medical information module.

The medical network 50 connects a patient 10 with a physician 12, a pharmacist 14, an insurance provider 20, a clinical laboratory 22, and an application provider 24. The patient 10 accesses the medical network 50 via a patient device 30. The physician 12 accesses the medical network 50 via a physician device 32. The pharmacist 14 accesses the medical network 50 via a pharmacist device 34. The medical network 50 provides for communication within a telehealth module 75, as shown in FIG. 2. The medical network 50 provides for communication within a medical information module 77 and the sharing of patient data 79, as shown in FIG. 5.

Figure 3:
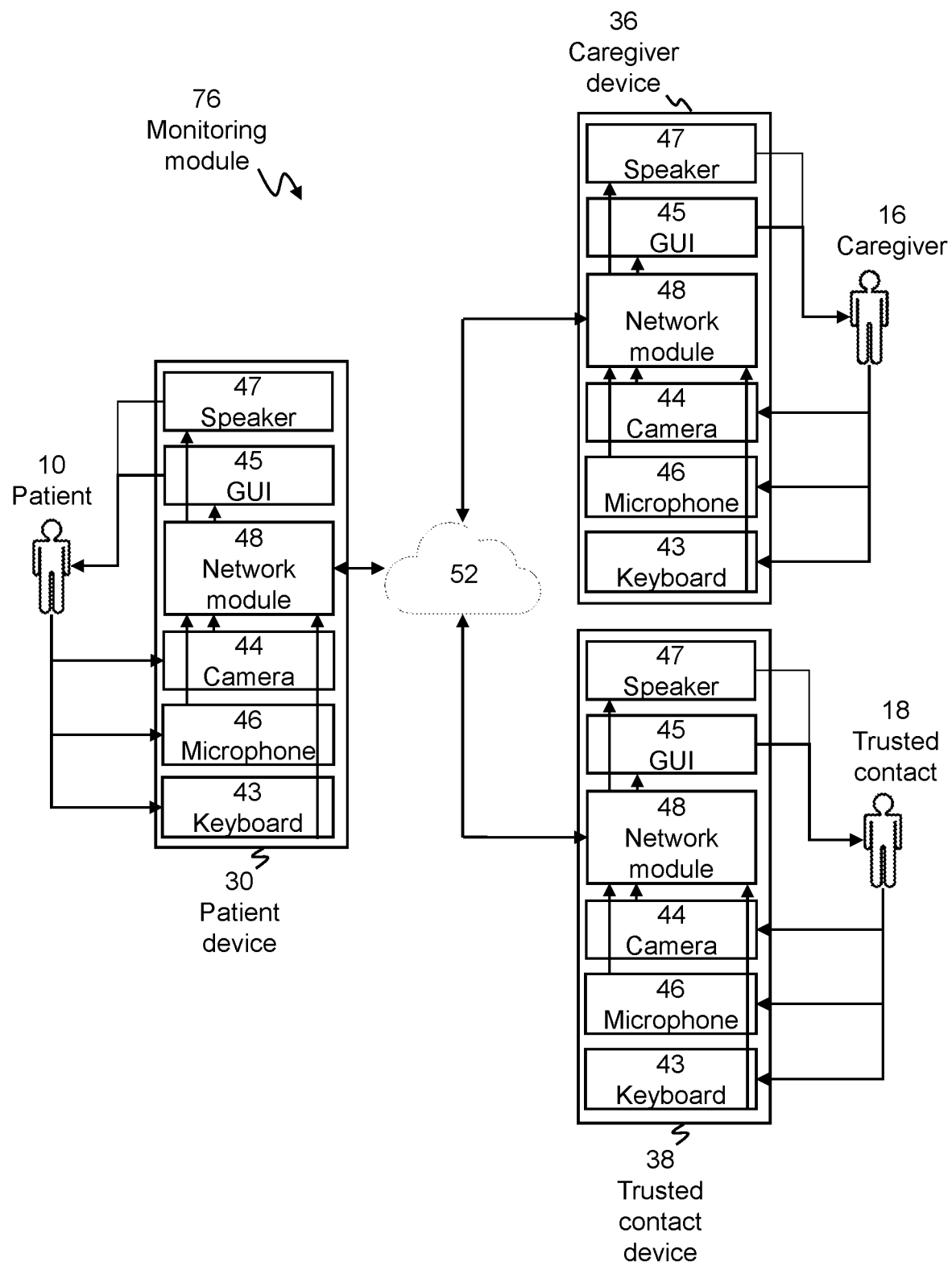
FIG. 3 is a schematic of a monitoring module.

The personal network 52 connects a patient 10 with a caregiver 16 and a trusted contact 18. The patient 10 accesses the personal network 52 via a patient device 30. The caregiver 16 accesses the personal network 52 via a caregiver device 36. The trusted contact 18 accesses the personal network 52 via a trusted contact device 38. The personal network 52 provides for communication within a monitoring module 76, as shown in FIG. 3.

The back-end network 54 connects an application provider 24 to a third-party application provider 26.

FIG. 2 is a schematic of a telehealth module 75. The telehealth module 75 includes a medical network 50, a patient device 30, a physician device 32, and a pharmacist device 34. A patient 10, a physician 12, and a pharmacist 14 can communicate via their respective devices 30, 32, 34 with each other through the medical network 50.

The patient device 30 includes a speaker 47, a graphical user interface ("GUI") 45, a network module 48, a camera 44, a microphone 46, and a keyboard 43. The camera 44, the microphone 46, and the keyboard 43 of the patient device 30 receive data from the patient 10 and the data is communicated to the medical network 50 via the network module 48 of the patient device 30. The network module 48 of the patient device 30 receives data from the medical network 50 and the data is communicated to the patient 10 via the speaker 47 and the GUI 45 of the patient device 30.

The physician device 32 includes a speaker 47, a graphical user interface ("GUI") 45, a network module 48, a camera 44, a microphone 46, and a keyboard 43. The camera 44, the microphone 46, and the keyboard 43 of the physician device 32 receive data from the physician 12 and the data is communicated to the medical network 50 via the network module 48 of the physician device 32. The network module 48 of the physician device 32 receives data from the medical network 50 and the data is communicated to the physician 12 via the speaker 47 and the GUI 45 of the physician device 32.

The pharmacist device 34 includes a speaker 47, a graphical user interface ("GUI") 45, a network module 48, a camera 44, a microphone 46, and a keyboard 43. The camera 44, the microphone 46, and the keyboard 43 of the pharmacist device 34 receive data from the pharmacist 12 and the data is communicated to the medical network 50 via the network module 48 of the pharmacist device 34. The network module 48 of the pharmacist device 34 receives data from the medical network 50 and the data is communicated to the pharmacist 12 via the speaker 47 and the GUI 45 of the pharmacist device 34.

FIG. 3 is a schematic of a monitoring module 76. The monitoring module 76 includes a personal network 52, a patient device 30, a caregiver device 36, and a trusted contact device 38. A patient 10, a caregiver 16, and a trusted contact 18 can communicate via their respective devices 30, 36, 38 with each other through the personal network 52.

The patient device 30 includes a speaker 47, a graphical user interface ("GUI") 45, a network module 48, a camera 44, a microphone 46, and a keyboard 43. The camera 44, the microphone 46, and the keyboard 43 of the patient device 30 receive data from the patient 10 and the data is communicated to the personal network 52 via the network module 48 of the patient device 30. The network module 48 of the patient device 30 receives data from the personal network 52 and the data is communicated to the patient 10 via the speaker 47 and the GUI 45 of the patient device 30.

The caregiver device 36 includes a speaker 47, a graphical user interface ("GUI") 45, a network module 48, a camera 44, a microphone 46, and a keyboard 43. The camera 44, the microphone 46, and the keyboard 43 of the caregiver device 36 receive data from the caregiver 16 and the data is communicated to the personal network 52 via the network module 48 of the caregiver device 36. The network module 48 of the caregiver device 36 receives data from the personal network 52 and the data is communicated to the caregiver 16 via the speaker 47 and the GUI 45 of the caregiver device 36.

The trusted contact device 38 includes a speaker 47, a graphical user interface ("GUI") 45, a network module 48, a camera 44, a microphone 46, and a keyboard 43. The camera 44, the microphone 46, and the keyboard 43 of the trusted contact device 38 receive data from the trusted contact 18 and the data is communicated to the personal network 52 via the network module 48 of the trusted contact device 38. The network module 48 of the trusted contact device 38 receives data from the personal network 52 and the data is communicated to the trusted contact 18 via the speaker 47 and the GUI 45 of the trusted contact device 38.

Figure 4:
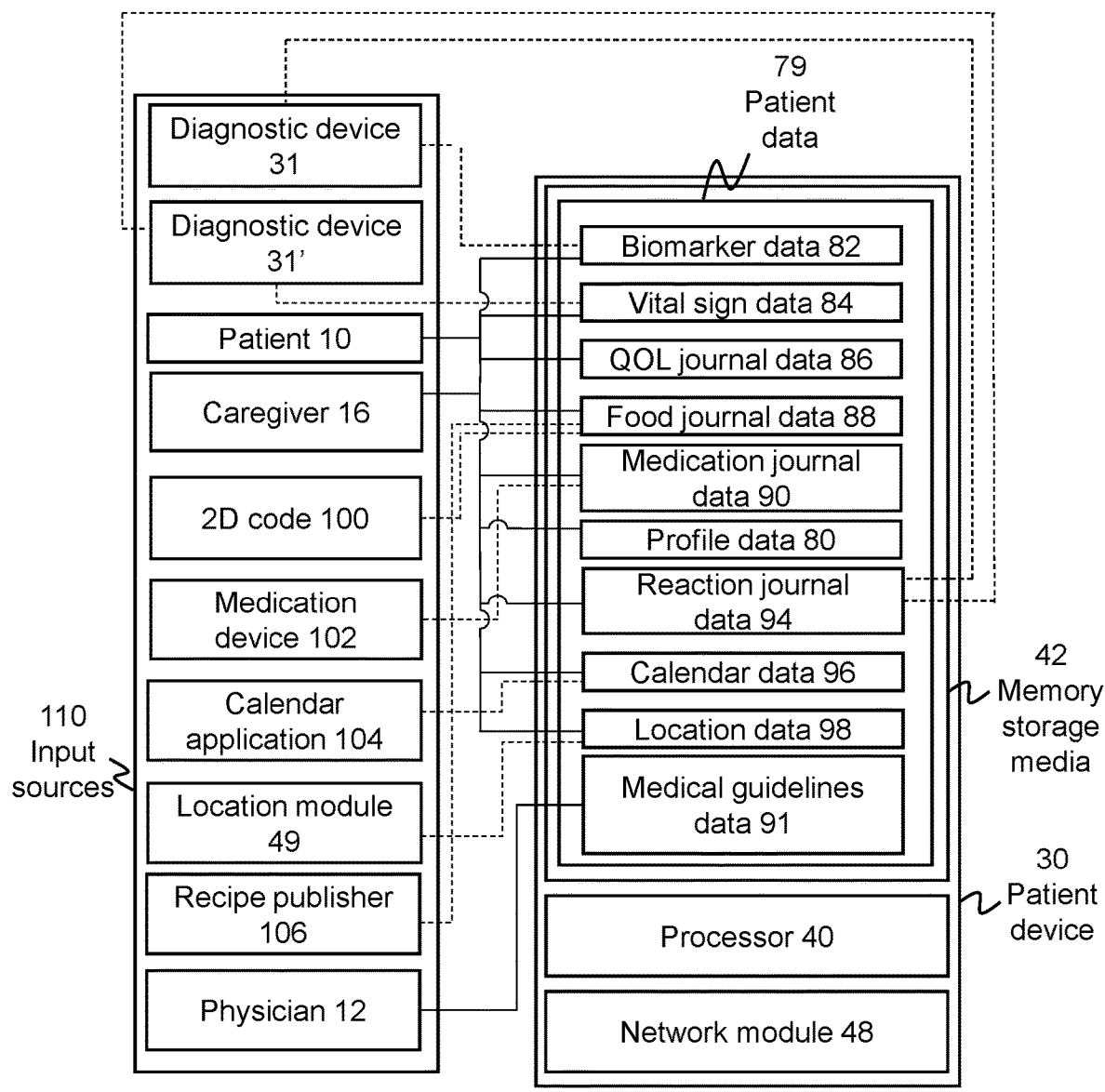
FIG. 4 is a schematic of patient data and associated input sources.

FIG. 4 is a schematic of patient data 79 and associated input sources 110. The input sources 110 transmit data autonomously, denoted by dashed lines, or manually, denoted by solid lines. The patient data 79 is stored in a memory storage media 42 located in the patient device 30. The patient data 79 can be communicated from the patient device 30 to physicians, pharmacies, clinical laboratories, and/or insurance providers via a medical network 50, as shown in FIG. 5. The patient data 79 can be received from and/or communicated to a caregiver device 36 via a personal network 52, as shown in FIG. 5. The communication between the patient device 30 and a medical network 50 and/or a personal network 52 may be performed via a network module 48. A processor 40 of the patient device 30 may perform various functions with the patient data 79.

A diagnostic device 31 provides biomarker data 82 and reaction journal data 94. A diagnostic device 31' provides vital sign data 84 and reaction journal data 94 to the patient device 30. The patient 10 provides biomarker data 82, vital sign data 84, quality of life ("QOL") journal data 86, food journal data 88, medication journal data 90, profile data 80, reaction journal data 94, calendar data 96, and location data 98 to the patient device 30. The caregiver 16 provides biomarker data 82, vital sign data 84, QOL data 86, food journal data 88, medication journal data 90, profile data 80, reaction journal data 94, calendar data 96, and location data 98 to the patient device 30. The 2D code reader application 100 provides food journal data 88 to the patient device 30. The medication device 102 provides medication journal data 90 to the patient device 30. The calendar application 104 provides calendar data 96 to the patient device 30. The location module 49 provides location data 98 to the patient device 30. The recipe publisher 106 provides food journal data 88 to the patient device 30. The physician 12 provides medical guideline data 91 to the patient device 30.

FIG. 5 is a schematic of a medical information module 77. The medical information module 77 includes an insurance provider database 64, a clinical laboratory database 72, a pharmacy database 62, a physician database 60, an application provider database 68, a medical network 50, a personal network 52, a patient device 30, and a caregiver device 36. The patient device 30 communicates patient data 79, via the medical network 50 to the insurance provider database 64, the clinical laboratory database 72, the pharmacy database 62, the physician database 60, and the application provider database 68. The patient device 30 receives data from the insurance provider database 64, the clinical laboratory database 72, the pharmacy database 62, the physician database 60, and the application provider database 68. The patient device 30 receives patient data 79 from the caregiver device 36 via the personal network 52.

Figure 6A:
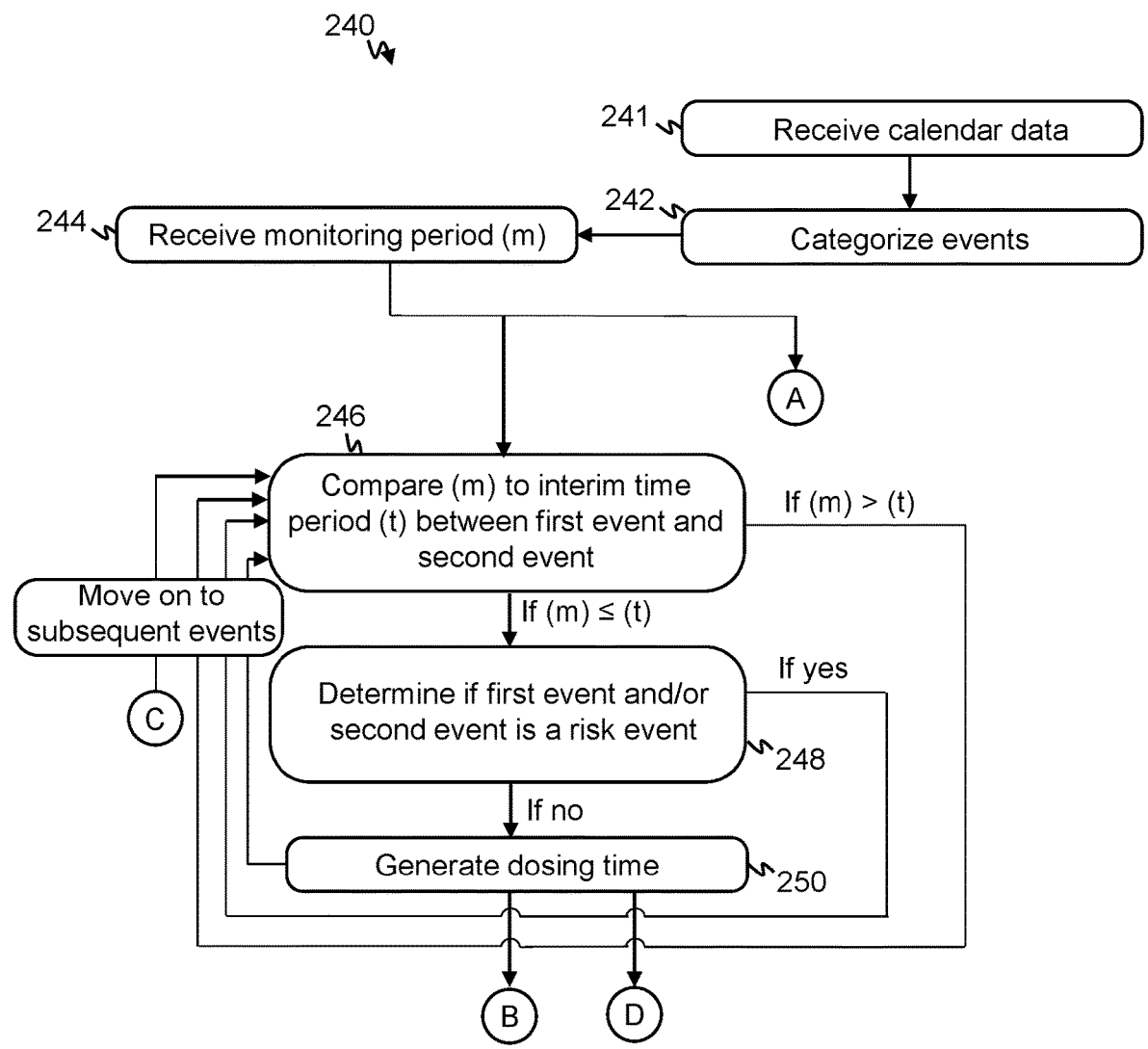
FIG. 6A is a flowchart of a method according to the present disclosure.

FIG. 6A is a flowchart of a method 240 for suggesting a dosing time based upon an interim period between events. A patient device receives calendar data 96 at step 240. The calendar data 96 includes events 161 and event time periods 162 associated with the events 161, as shown in FIG. 6E. The patient device then categorizes events 161 included in the calendar data 96 at step 242. The patient device receives a monitoring period (m) at step 244. The patient device compares the monitoring period (m) to an interim time period (t) 163, as shown in FIG. 6E, between a first event and a second event at step 246. If the monitoring period (m) is greater than the interim time period (t) 163, then the comparing step 246 is repeated for subsequent events 161 (e.g., the second event and a third event). If the monitoring period (m) is less than or equal to the interim time period (t) 163, then the patient device determines if the first event and/or the second event is a risk event at step 248. If the first event and/or the second event is a risk event, then the comparing step 246 is repeated for subsequent events 161. If the first event and/or the second event is not a risk event, then the patient device generates a dosing time at step 250.

Figure 6B:
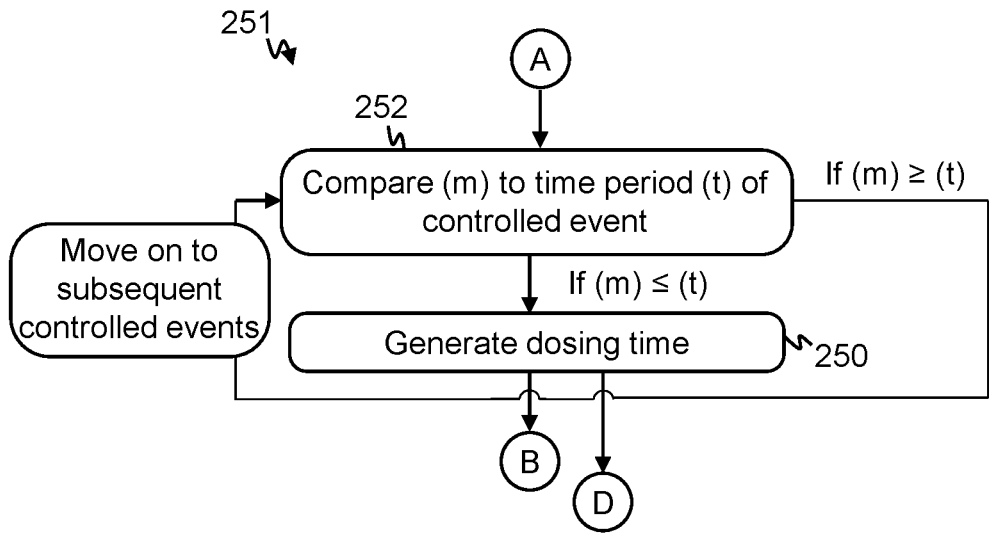
FIG. 6B is a flowchart of a method according to the present disclosure.

FIG. 6B is a flowchart of a method 251 for suggesting a dosing time based upon a controlled event. The method 251 follows from the method 240, as shown in FIG. 6A. A patient device compares a monitoring period (m) to an event time period 162 of a controlled event 168, as shown in FIG. 6E, at step 252. If the monitoring period (m) is greater than the event time period 162 of the controlled event 168, then the comparing step 252 is repeated for subsequent controlled events 168. If the monitoring period (m) is less than or equal to an event time period 162 of a controlled event 168, then the patient device generates a dosing time at step 250.

Figure 6C:
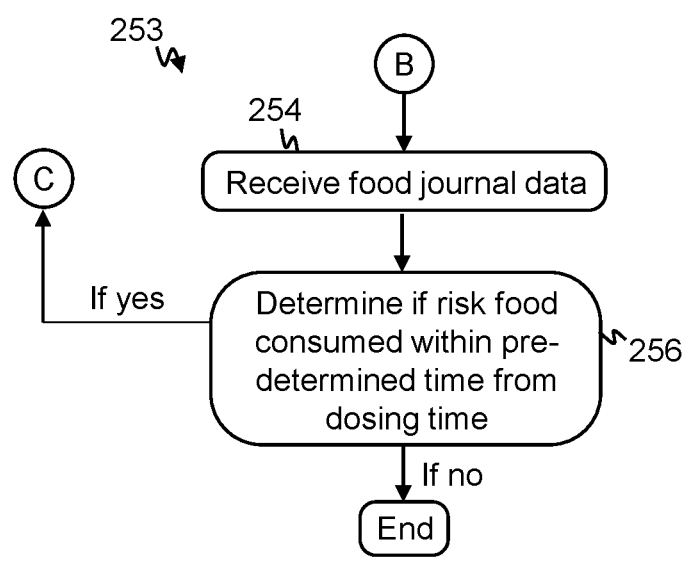
FIG. 6C is a flowchart of a method according to the present disclosure.
Figures 6D, 6E:
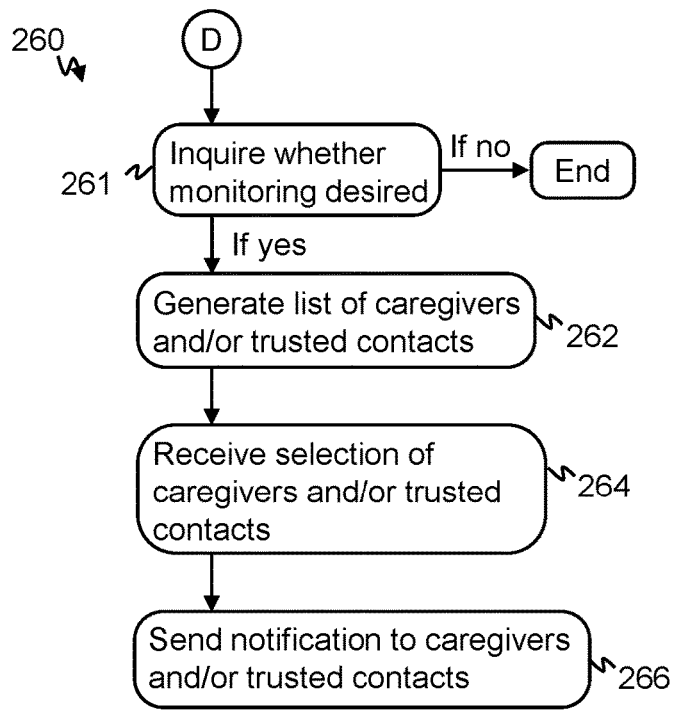
FIG. 6D is a flowchart of a method according to the present disclosure.
FIG. 6E illustrates calendar data.

FIG. 6C is a flowchart of a method 253 for adjusting a dosing time based upon food journal data. The method 253 follows from the method 240 or the method 251, as shown in FIG. 6A or 6B, respectively. A patient device receives food journal data at step 254. The patient device then determines if a risk food has been consumed within a pre-determined time from the dosing time at step 256. If a risk food has been consumed within a pre-determined time from the dosing time, then the comparing step 246, as shown in FIG. 6A, is repeated for subsequent events. If a risk food has not been consumed within a pre-determined time from the dosing time, then the prior determined dosing time remains.

FIG. 6D is a flowchart of a method 260 for notifying caregivers and/or trusted contacts that monitoring is desired. The method 260 follows from the method 240 or the method 251, as shown in FIG. 6A or 6B, respectively. A patient device inquires the patient whether monitoring is desired at step 261. If monitoring is not desired, then no further action is taken. If monitoring is desired, then the patient device generates a list of caregivers and/or trusted contacts at step 262. Then the patient device receives, from the patient, a selection of caregivers and/or trusted contacts at step 264. Then the patient device sends a notification, at step 266, to caregivers and/or trusted contacts selected by the patient.

FIG. 6E illustrates calendar data 96. The calendar data includes event entries 160. Each event entry 160 includes events 161, categories 164, and event time periods 162. An interim time period 163 is illustrated between event entries 160. The categories 164 associated with the events 161 include occupied events 172, a risk event 170, and a controlled event 168.

Figure 7:
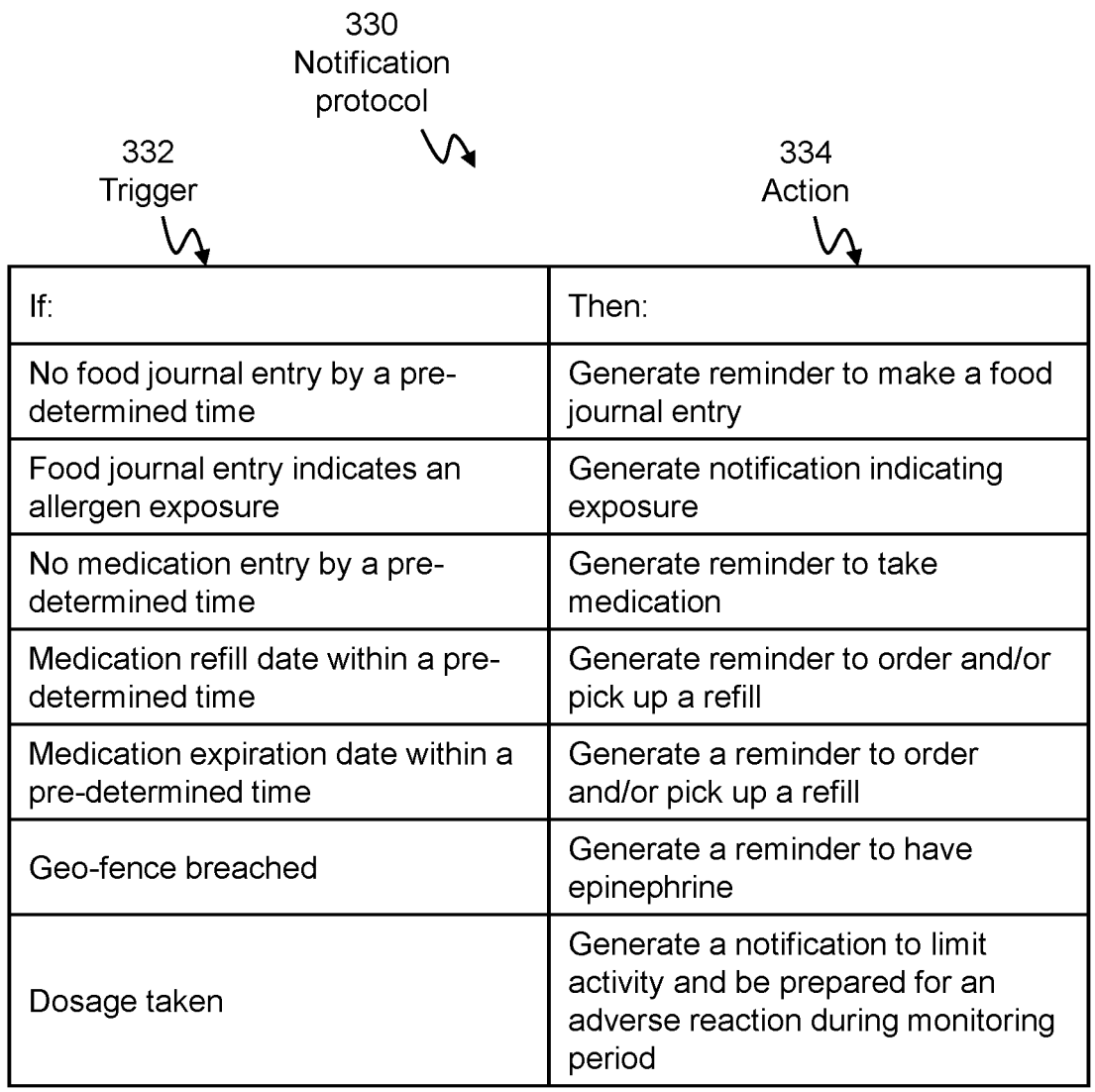
FIG. 7 is a table of a notification protocol.

FIG. 7 is a table of a notification protocol 330. The notification protocol 330 includes triggers 332 and actions 334 that are initiated by the triggers 332.

Figure 8:
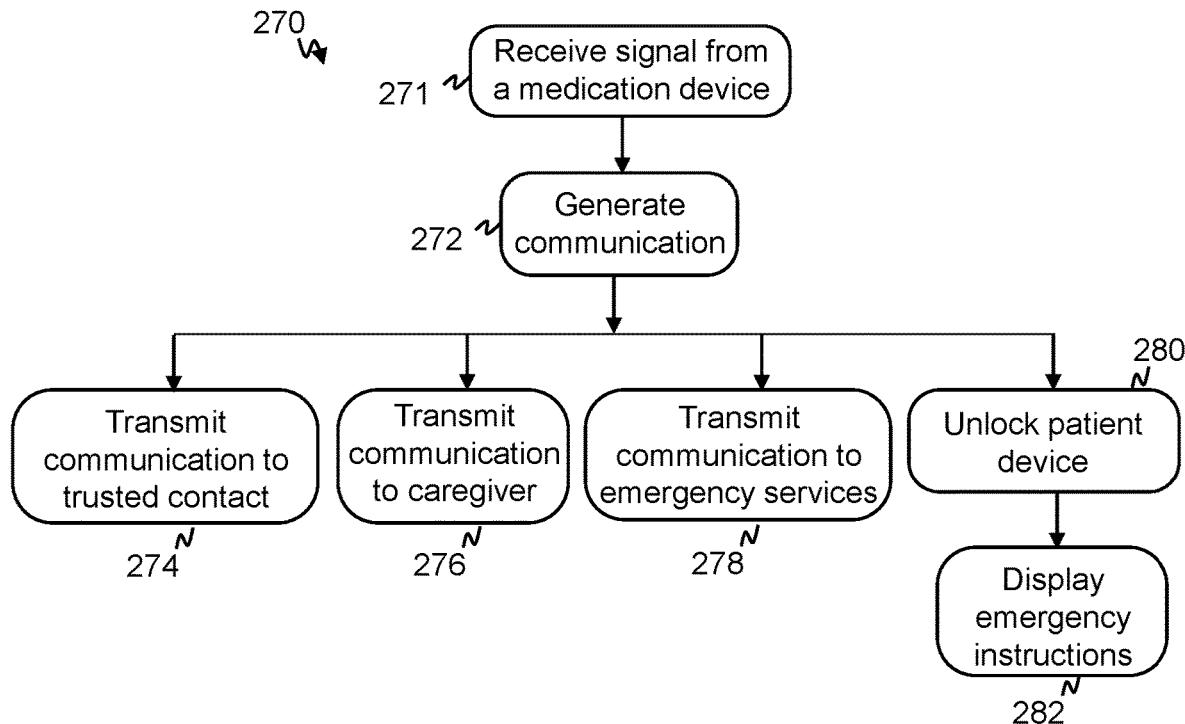
FIG. 8 is a flowchart of a method according to the present disclosure.

FIG. 8 is a flowchart of a method for a reaction response 270. A patient device receives a signal from a medication device at step 271. The patient device generates a communication at step 272. The communication of step 272 is then transmitted to a trusted contact at step 274, to a caregiver at step 276, and to emergency services at step 278. The patient device unlocks at step 280 and then displays emergency instructions at step 282. One or any combination of steps 274, 276, 278, 280, and 282 may occur as directed by the settings instructed by the patient and/or caregiver.

Figure 9:
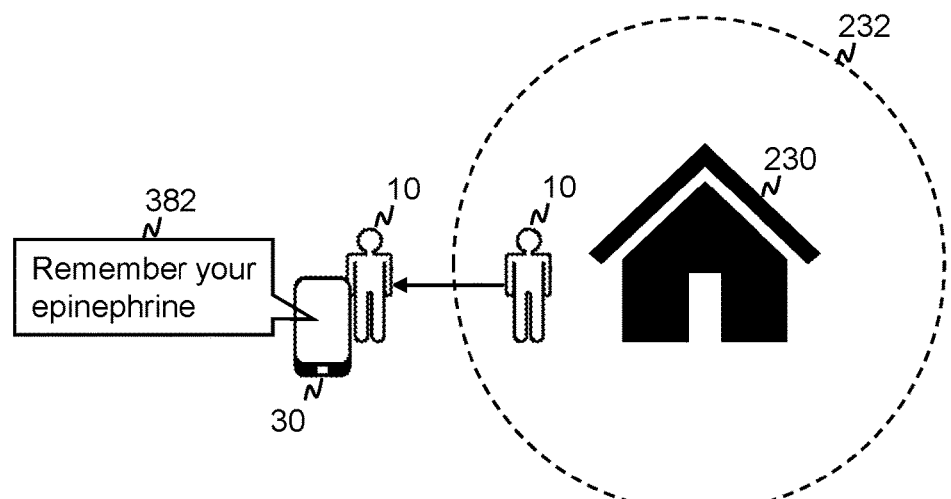
FIG. 9 is a schematic of a geo-fence system.

FIG. 9 is a schematic of a geo-fence 232. The geo-fence 232 surrounds a saved location 230. When a patient 10 crosses the geo-fence 232, a text message 382 is generated by the patient device 30. The text message 382 reminds the patient 10 to have epinephrine with them.

Figure 10:
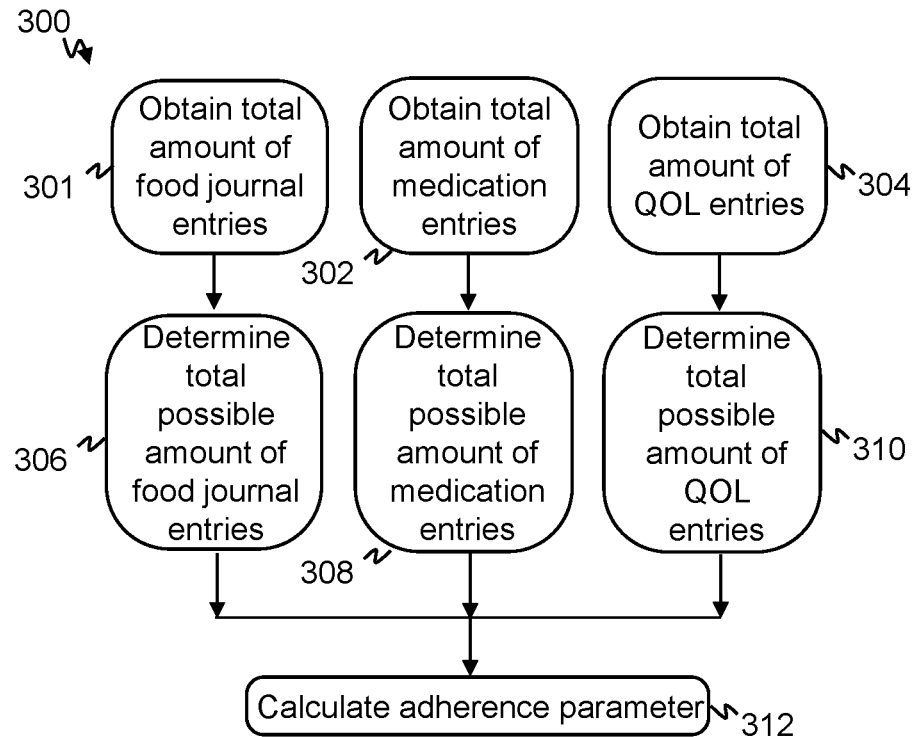
FIG. 10 is a flowchart of a method according to the present disclosure.

FIG. 10 is a flowchart of a method 300 for determining treatment adherence. The patient device obtains a total amount of food journal entries at step 301, a total amount of medication entries at step 302, and a total amount of quality of life ("QOL") entries at step 304. The patient device then determines the total possible amount of food journal entries at step 306, total possible amount of medication entries at step 308, and total possible amount of QOL entries at step 310. The patent device then calculates an adherence parameter at step 312.

Figure 11:
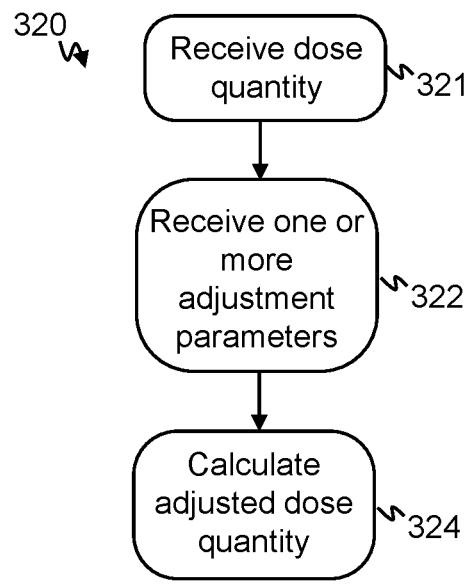
FIG. 11 is a flowchart of a method according to the present disclosure.

FIG. 11 is a flowchart of a method 320 for adjusting dosage. A patient device receives a dose quantity at step 321. The patient device then receives one or more adjustment parameters at step 322. The patient device then calculates an adjusted dose quantity at step 324.

Figures 12, 13A, 13B:
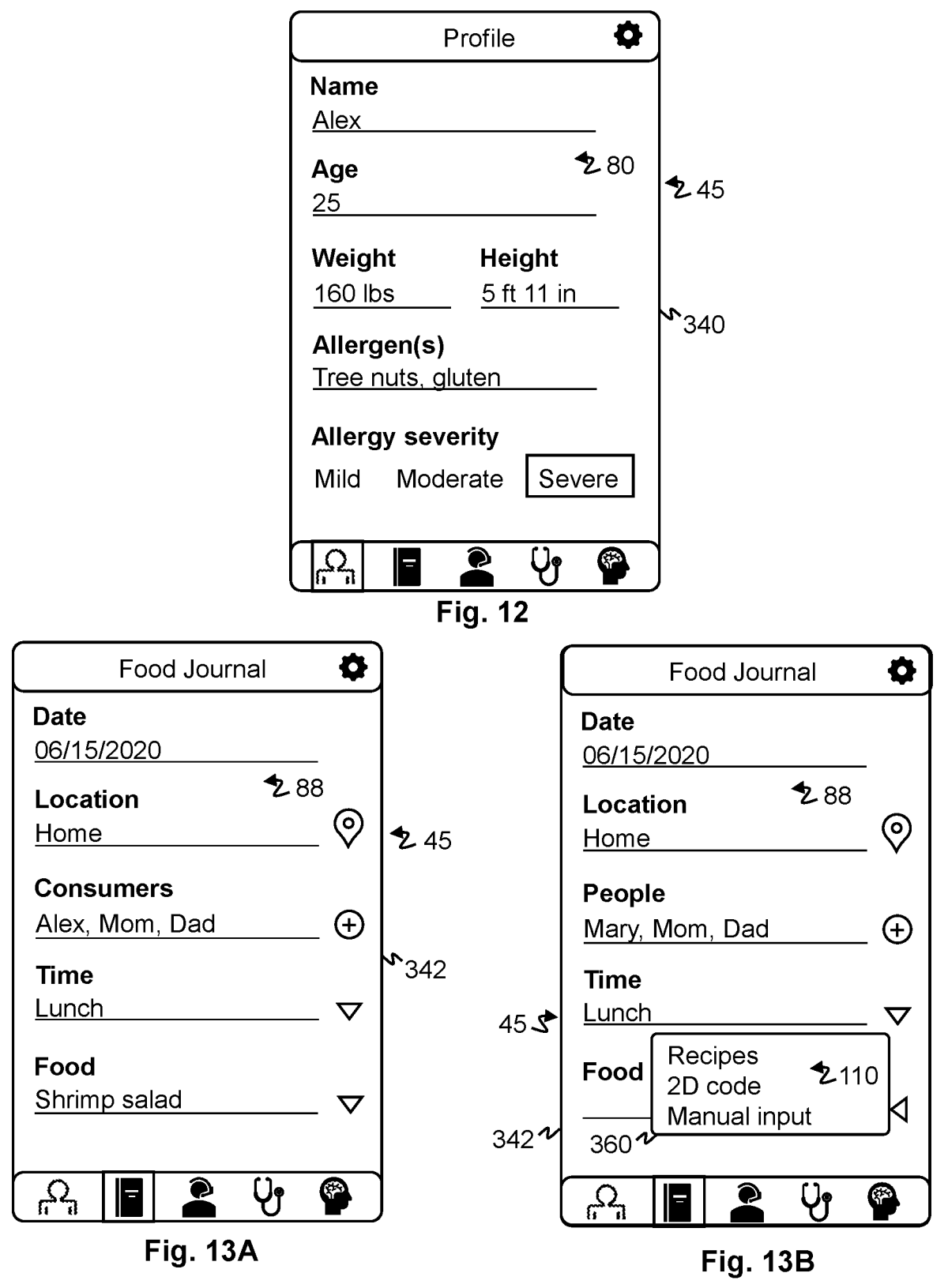

FIG. 12 illustrates a graphical user interface 45. The graphical user interface ("GUI") 45 displays a profile page 340. The profile page 340 includes profile data 80. The profile data 80 includes the patient's name, age, weight, height, allergens, and allergy severity. The profile data 80 is input by a patient 10 and/or a caregiver 16, as shown in FIG. 4.

FIG. 13A and FIG. 13B illustrates a graphical user interface 45. The graphical user interface ("GUI") 45 displays a food journal page 342. The food journal page 342 includes food journal data 88. The food journal data 88 includes date, location, consumers, time, and food. The food journal data 88 is input by a patient 10, a caregiver 16, a 2D code reader application 100, or any combination thereof, as shown in FIG. 4. The food journal page 342 includes a sub-menu 360, as shown in FIG. 13B where an input source 110, as shown in FIG. 4, is selected.

Figure 13C:
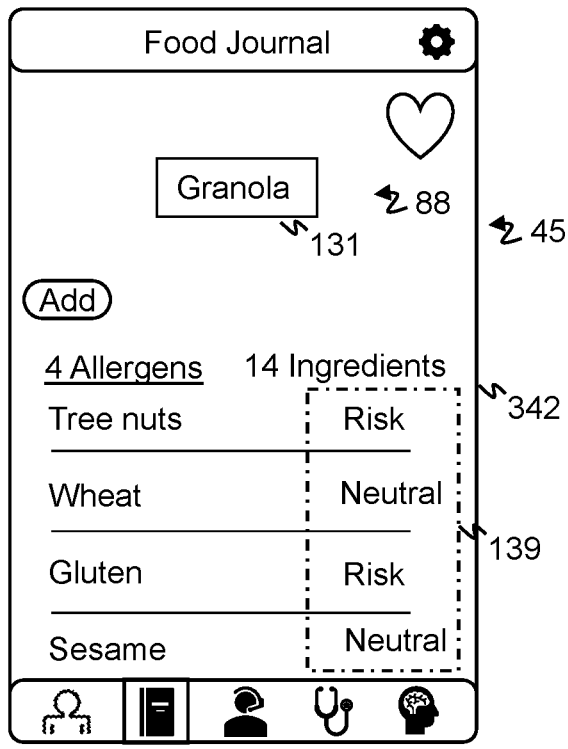
FIG. 13C illustrates a graphical user interface.

FIG. 13C illustrates a graphical user interface 45. The graphical user interface ("GUI") 45 displays a food journal page 342. The food journal page 342 includes food journal data 88 obtained by a 2D code reader application 100, as shown in FIG. 4. The food journal data 88 includes a food 131 and food categories 139. The food categories 139 indicate whether the food 131 is a risk food or a neutral food, in association with the allergens identified in the profile page 340, as shown in FIG. 12.

Figure 13D:
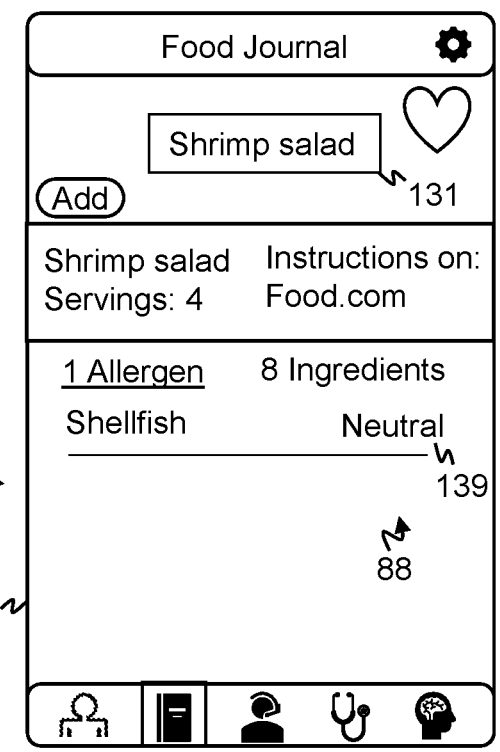
FIG. 13D illustrates a graphical user interface.

FIG. 13D illustrates a graphical user interface 45. The graphical user interface ("GUI") 45 displays a food journal page 342. The food journal page 342 includes food journal data 88 obtained by a recipe publisher 106, as shown in FIG. 4. The food journal data 88 includes a food 131 and a food category 139. The food category 139 indicates whether the food 131 is a risk food or a neutral food, in association with the allergens identified in the profile page 340, as shown in FIG. 12A.

Figure 14:
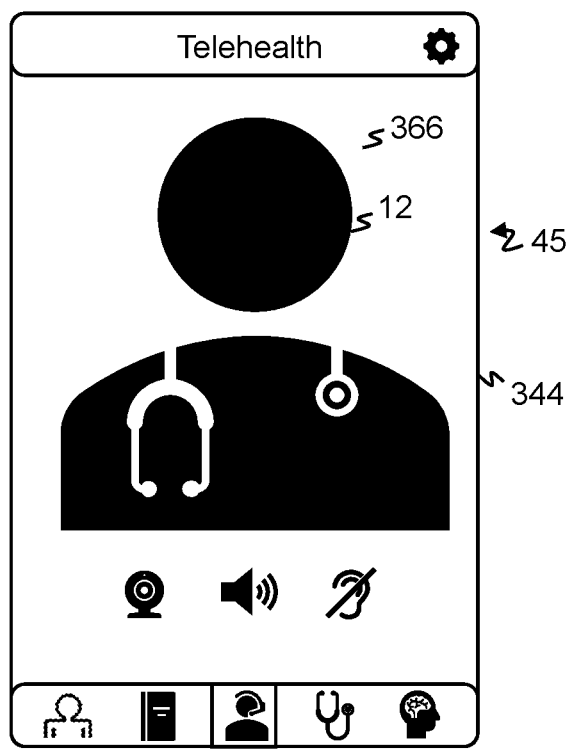
FIG. 14 illustrates a graphical user interface.

FIG. 14 illustrates a graphical user interface 45. The graphical user interface ("GUI") 45 displays a telehealth page 344. The telehealth page 344 shows a video display 366 of a physician 12 enabled by the telehealth module 75, as shown in FIG. 2.

Figure 15:
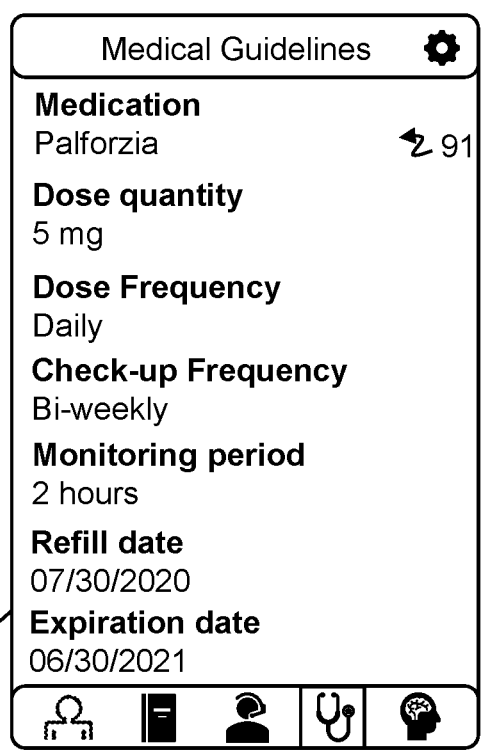
FIG. 15 illustrates a graphical user interface.

FIG. 15 illustrates a graphical user interface 45. The graphical user interface ("GUI") 45 displays a medical guidelines page 346. The medical guidelines page 346 includes medical guidelines data 91 obtained from a physician 12, as shown in FIG. 4. The medical guidelines data 91 includes medication, dose quantity, dose frequency, monitoring period, refill date, and expiration date.

Figures 16, 17, 18:
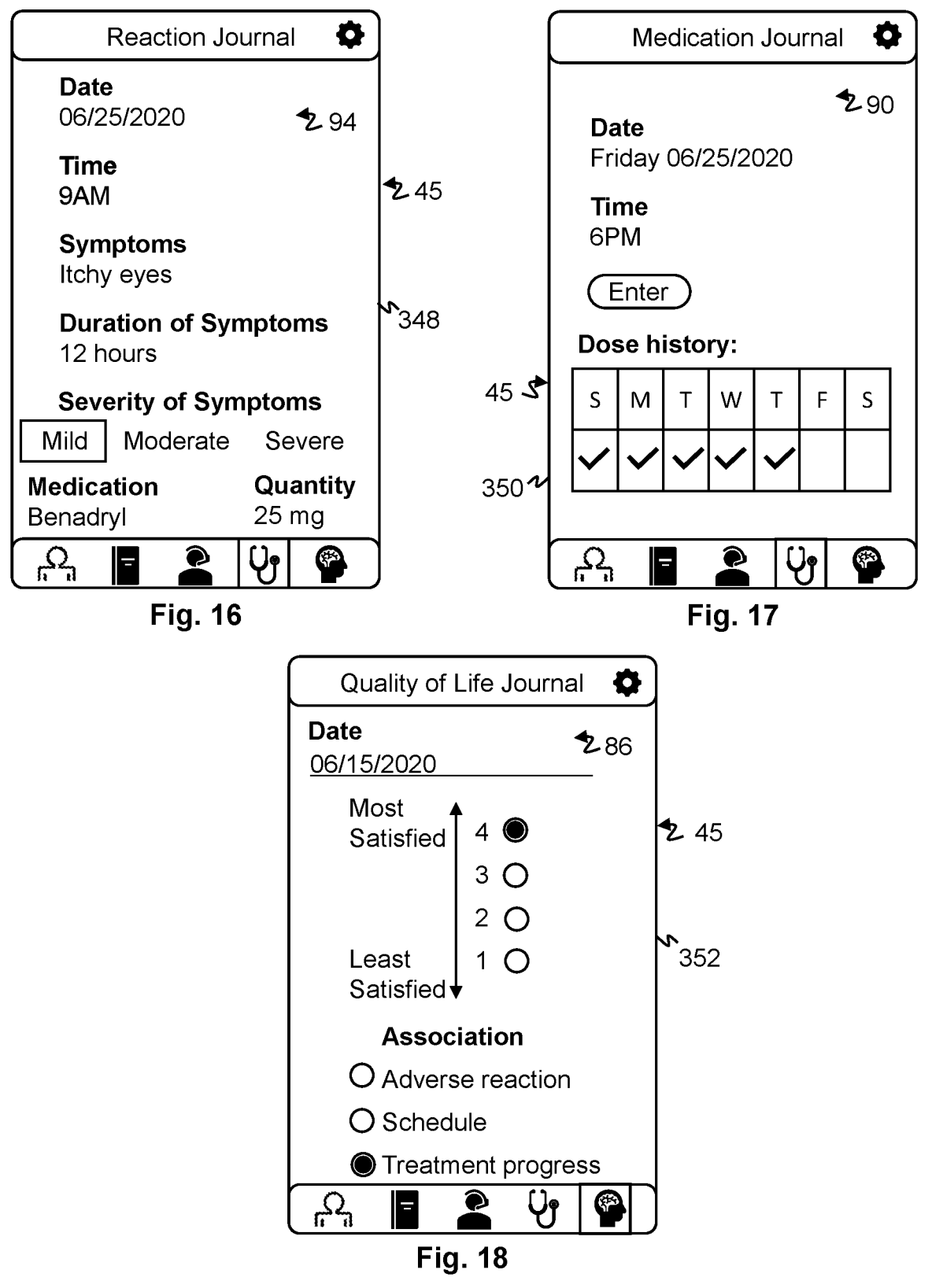

FIG. 16 illustrates a graphical user interface 45. The graphical user interface ("GUI") 45 displays a reaction journal page 348. The reaction journal page 348 includes reaction journal data 94 obtained from a patient 10 and/or caregiver 16, as shown in FIG. 4. The reaction journal data 94 includes date, time, symptoms, duration of symptoms, severity of symptoms, reaction medication, and reaction medication quantity.

FIG. 17 illustrates a graphical user interface 45. The graphical user interface ("GUI") 45 displays a medication journal page 350. The medical journal page 350 includes medication journal data 90 obtained from a patient 10, a caregiver 16, a medication device 102, or any combination thereof, as shown in FIG. 4. The medication journal data 90 includes the date and time the medication is taken as well as a dose history indicating the days a dose was taken.

FIG. 18 illustrates a graphical user interface 45. The graphical user interface ("GUI") 45 displays a quality of life ("QOL") journal page 352. The QOL journal page 352 includes QOL journal data 86 obtained from a patient 10 and/or a caregiver 16. The QOL journal data 86 includes a date on which the entry is made, a QOL metric, and an association of the patient's experience to the QOL metric.

Any numerical values recited in the above application include all values from the lower value to the upper value in increments of one unit provided that there is a separation of at least 2 units between any lower value and any higher value. These are only examples of what is specifically intended and all possible combinations of numerical values between the lowest value and the highest value enumerated are to be considered to be expressly stated in this application in a similar manner. Unless otherwise stated, all ranges include both endpoints and all numbers between the endpoints.

The terms "generally" or "substantially" to describe angular measurements may mean about +/−10° or less, about +/−5° or less, or even about +/−1° or less. The terms "generally" or "substantially" to describe angular measurements may mean about +/−0.01° or greater, about +/−0.1° or greater, or even about +/−0.5° or greater. The terms "generally" or "substantially" to describe linear measurements, percentages, or ratios may mean about +/−10% or less, about +/−5% or less, or even about +/−1% or less. The terms "generally" or "substantially" to describe linear measurements, percentages, or ratios may mean about +/−0.01% or greater, about +/−0.1% or greater, or even about +/−0.5% or greater.

The term "consisting essentially of" to describe a combination shall include the elements, ingredients, components, or steps identified, and such other elements ingredients, components or steps that do not materially affect the basic and novel characteristics of the combination. The use of the terms "comprising" or "including" to describe combinations of elements, ingredients, components, or steps herein also contemplates embodiments that consist essentially of the elements, ingredients, components, or steps.

Plural elements, ingredients, components, or steps can be provided by a single integrated element, ingredient, component, or step. Alternatively, a single integrated element, ingredient, component, or step might be divided into separate plural elements, ingredients, components, or steps. The disclosure of "a" or "one" to describe an element, ingredient, component, or step is not intended to foreclose additional elements, ingredients, components, or steps.

Terms provided at the beginning of a list may be distributive to each item in the list unless otherwise indicated.

REFERENCE NUMERALS

10—Patient ("user"); 12—Physician; 14—Pharmacist; 16—Caregiver; 18—Trusted contact; 20—Insurance provider; 22—Clinical laboratory; 24—Application provider; 26—Third-party application provider; 30—Patient device; 31—Diagnostic device; 32—Physician device; 34—Pharmacist device; 36—Caregiver device; 38—Trusted contact device; 40—Processor; 42—Memory storage media; 43—Keyboard; 44—Camera; 45—Graphical user interface ("GUI"); 46—Microphone; 47—Speaker; 48—Network module; 49—Location module; 50—Medical network; 52—Personal network; 54—Back-end network; 60—Physician database; 62—Pharmacy database; 64—Insurance provider database; 68—Application provider database; 72—Clinical laboratory database; 74—Treatment management system; 75—Telehealth module; 76—Monitoring module; 77—Medical information module; 79—Patient data; 80—Profile data; 82—Biomarker data; 84—Vital sign data; 86—QOL journal data; 88—Food journal data; 90 Medication journal data; 91—Medical guidelines data; 94—Reaction journal data; 96—Calendar data; 98—Location data; 100—2D code reader application; 102—Medication device; 104—Calendar application; 106—Recipe publisher; 110—Input source; 131—Food; 139—Food category; 230—Saved location; 232—Geo-fence; 340—Profile page; 342—Food journal page; 344—Telehealth page; 346—Medical guidelines page; 348—Reaction journal page; 350—medication journal page; 352—QOL journal page; 366—video display; 382—Text message.

What is claimed is:

1. A system for managing food allergy immunotherapy comprising:
 a patient device and a physician device, each including: a user interface, a network module; and a processor; and a medical network;
  wherein the patient device receives inputs, via the user interface, of patient data including food journal data, quality of life data, and medication data;
  wherein the patient device and/or the physician device calculates, via their respective processors, a medication adjustment parameter from the patient data, the medication adjustment parameter including an increased dosage quantity, a decreased dosage quantity, an increased dosage frequency, a decreased dosage frequency, or any combination thereof;
  wherein the patient device digitally transmits, via the network modules of the respective devices, the patient data and/or the medication adjustment parameter to the physician device; and
  wherein the medication data and the medication adjustment parameter are associated with oral immunotherapy medication; and
  wherein the patient data is transmitted to the physician device in real-time, upon the patient device connecting to the medical network, upon the patient device syncing with one or more remote devices, upon a user input, or any combination thereof.

2. The system of claim 1, wherein compliance with the food allergy immunotherapy is determined from the patient data.

3. The system of claim 1, further comprising a pharmacist device, a caregiver device, a trusted contact device, or any combination thereof.

4. The system of claim 3, wherein the caregiver device, the trusted contact device, or both transmit and/or receive data to and/or from the patient device over a personal network, via a network module, respectfully thereof.

5. The system of claim 4, wherein one or more caregivers, one or more trusted contacts, or both monitor a patient via the caregiver device, the trusted contact device, or both, respectively upon the patient medicating with the oral immunotherapy medication.

6. The system of claim 5, wherein the one or more remote devices include one or more cloud servers.

7. The system of claim 1, wherein the patient data is stored on one or more memory storage media of the patient device, one or more memory storage media of the physician device, one or more memory storage media of the one or more remote devices, or any combination thereof.

8. The system of claim 1, wherein the patient data is transmitted from the patient device to the physician device, over the medical network, via the one or more network modules.

9. The system of claim 1, wherein the patient data further includes calendar data; and wherein a dosing time is determined based upon risk events in the calendar data and a monitoring period that occurs after the dosing time.

10. The system of claim 9, wherein the dosing time is adjusted based at least in part on the food journal data.

11. The system of claim 10, wherein the dosing time is adjusted from a previously scheduled dosing time if the food journal data indicates that a risk food has been consumed within a pre-determined time from the previously scheduled dosing time.

12. A non-transitory computer-readable storage medium storing an application, the computer-readable storage medium comprising instructions for a method for managing food allergy immunotherapy comprising:
    receiving, by a patient device, via a user interface of the patient device, patient data including food journal data, quality of life data, and medication data;
    calculating, by a processor of the patient device and/or a second device, a medication adjustment parameter as a function of the patient data, the medication adjustment parameter including an increased dosage quantity, a decreased dosage quantity, an increased dosage frequency, a decreased dosage frequency, or any combination thereof; and
    wherein the medication data and the medication adjustment parameter are associated with oral immunotherapy medication.

13. The method of claim 12, wherein the method further includes the steps of:
    transmitting, by the patient device, the medication adjustment parameter to a physician device for the medication adjustment parameter to be approved by a physician;
    receiving, by the patient device, a signal indicating an approval by the physician.

14. The method of claim 13, wherein the medication adjustment parameter is calculated in real-time upon receiving the patient data, the medication adjustment parameter is calculated on a time interval, or both.

15. The method of claim 12, wherein the patient data further includes calendar data; and wherein a dosing time is determined based upon risk events in the calendar data and a monitoring period that occurs after dosing.

16. The method of claim 15, wherein the dosing time is adjusted based at least in part on the food journal data.

17. The method of claim 16, wherein the dosing time is adjusted from a previously scheduled dosing time if the food journal data indicates that a risk food has been consumed within a pre-determined time from the previously scheduled dosing time.

\* \* \* \* \*